(12) United States Patent
Togino

(10) Patent No.: US 8,254,038 B2
(45) Date of Patent: Aug. 28, 2012

(54) OPTICAL ELEMENT, OPTICAL SYSTEM HAVING THE SAME AND ENDOSCOPE USING THE SAME

(75) Inventor: Takayoshi Togino, Koganei (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 12/655,910

(22) Filed: Jan. 7, 2010

(65) Prior Publication Data

US 2010/0110564 A1  May 6, 2010

Related U.S. Application Data

(63) Continuation of application No. PCT/JP2008/062663, filed on Jul. 8, 2008.

(30) Foreign Application Priority Data

Jul. 9, 2007 (JP) ................................. 2007-180150
Jul. 9, 2007 (JP) ................................. 2007-180151

(51) Int. Cl.
*G02B 13/06* (2006.01)
*G02B 17/00* (2006.01)

(52) U.S. Cl. ......................... 359/725; 359/726; 359/731

(58) Field of Classification Search .................. 359/725, 359/726–732, 402, 403; 348/36, 38–39
See application file for complete search history.

(56) References Cited

U.S. PATENT DOCUMENTS

| | | | |
|---|---|---|---|
| 2,485,345 A * | 10/1949 | Ackerman ..................... | 359/731 |
| 3,505,465 A | 4/1970 | Rees | |
| 5,745,302 A * | 4/1998 | Ohno ............................. | 359/689 |
| 5,854,713 A | 12/1998 | Kuroda et al. | |
| 5,930,055 A * | 7/1999 | Eisenberg ..................... | 359/728 |
| 6,115,193 A | 9/2000 | Shu | |
| 6,175,454 B1 | 1/2001 | Hoogland et al. | |
| 6,204,978 B1 * | 3/2001 | Akiyama et al. .............. | 359/729 |
| 6,356,296 B1 | 3/2002 | Driscoll, Jr. et al. | |
| 6,392,687 B1 | 5/2002 | Driscoll, Jr. et al. | |
| 6,449,103 B1 | 9/2002 | Charles | |
| 6,597,520 B2 | 7/2003 | Wallerstein et al. | |
| 6,611,282 B1 * | 8/2003 | Trubko et al. ................... | 348/36 |
| 7,019,918 B2 * | 3/2006 | Wallerstein et al. .......... | 359/725 |
| 7,570,437 B2 * | 8/2009 | Gal et al. ........................ | 359/725 |
| 2004/0254424 A1 | 12/2004 | Simkulet et al. | |
| 2005/0117227 A1 * | 6/2005 | Gal et al. ........................ | 359/725 |

(Continued)

FOREIGN PATENT DOCUMENTS

JP              60-42728         3/1985

(Continued)

*Primary Examiner* — Jordan Schwartz

(74) *Attorney, Agent, or Firm* — Kenyon & Kenyon LLP

(57) ABSTRACT

An optical element is made of a transparent medium that is rotationally symmetric relative to the central axis with a refractive index greater than 1. The transparent medium has a first transmissive surface at the outermost periphery relative to the central axis, a first reflective surface at the side of the central axis relative to the first transmissive surface, a second reflective surface at the side opposite to the image plane relative to the first reflective surface and a second transmissive surface at the side of the image plane relative to the second reflective surface. The flux of light enters and proceeds through the transparent medium via the first transmissive surface, the first reflective surface, the second reflective surface and the second transmissive surface to form an optical path. The optical path is formed only at a side relative to the central axis.

22 Claims, 28 Drawing Sheets

U.S. PATENT DOCUMENTS

2006/0114575 A1* 6/2006 Togino .................... 359/725

FOREIGN PATENT DOCUMENTS

| | | |
|---|---|---|
| JP | 2001-174713 | 6/2001 |
| JP | 2002-523801 | 7/2002 |
| JP | 2002-341409 | 11/2002 |
| JP | 2003-167193 | 6/2003 |
| JP | 2005-148265 | 6/2005 |
| JP | 2006-058412 | 3/2006 |
| JP | 2006-113096 | 4/2006 |
| JP | 2006-126322 | 5/2006 |
| JP | 2006-154364 | 6/2006 |
| JP | 2006-209041 | 8/2006 |
| JP | 2006-259659 | 9/2006 |
| JP | 2006-276816 | 10/2006 |
| WO | WO 2003-042743 | 5/2003 |
| WO | 2005-110186 | 11/2005 |

* cited by examiner (Y-direction)　　　　　　　　　　(X-direction)

(0.00°, 89.0°)

(0.00°, 63.0°)

(0.00°, 36.0°)

(0.00°, −89.0°)

(0.00°, −63.00°)

(0.00°, −36.00°)

(0.00°, 0.10°)

(a)

(b)

(c)

(a)

(b)

(c)

(a)

(b)

United States Patent US 8,254,038 B2

OPTICAL ELEMENT, OPTICAL SYSTEM HAVING THE SAME AND ENDOSCOPE USING THE SAME

This application is a continuation of PCT International Application No. PCT/JP 2008/062663 filed on Jul. 8, 2008, which designates the United States. A claim of priority and the benefit of the filing date under 35 U.S.C. §120 is hereby made to PCT International Application No. PCT/JP2008/062663 filed on Jul. 8, 2008, which in turn claims priority under 35 U.S.C. §119 to Japanese Application No. 2007-180150 filed on Jul. 9, 2007 and Japanese Application No. 2007-180151 filed on Jul. 9, 2007, each of which is expressly incorporated herein in its entirety by reference thereto.

BACKGROUND OF THE INVENTION AND RELATED ART STATEMENT

The present invention relates to an optical element, an optical system having such an optical element and an endoscope using such an optical system. More particularly, the present invention relates to an image formation optical system or a projection optical system having a function of forming an image around an axis of rotational symmetry as an annular image to an image pickup element.

Patent Document 1 listed below describes a known image pickup optical system having a refraction optical system, a reflection optical system and an image formation optical system arranged therein along with two optical paths so as to be capable of picking up a panoramic image and an axial image. Patent Document 2 describes a known endoscope similarly having two optical paths. Furthermore, Patent Document 3 describes a known endoscope by means of which it is possible to omni-directionally observe the surroundings and Patent Document 4 describes a known capsule endoscope by means of which it is also possible to omni-directionally observe the surroundings. Finally, Patent Document 5 describes an image pickup device that can shoot omni-directionally the surroundings and also only forward at the same time. Finally, Patent Documents 6 through 13 describe an omni-directional optical system.

[Patent Document 1] Jpn. PCT National Publication No. 2003-042743
[Patent Document 2] U.S. Patent Application Publication No. 2004-0254424
[Patent Document 3] JP-A-60-42728
[Patent Document 4] JP-A-2001-174713
[Patent Document 5] JP-A-2002-341409
[Patent Document 6] U.S. Pat. No. 3,505,465
[Patent Document 7] U.S. Pat. No. 5,854,713
[Patent Document 8] U.S. Pat. No. 6,115,193
[Patent Document 9] U.S. Pat. No. 6,175,454
[Patent Document 10] U.S. Pat. No. 6,356,296
[Patent Document 11] U.S. Pat. No. 6,392,687
[Patent Document 12] U.S. Pat. No. 6,449,103
[Patent Document 13] U.S. Pat. No. 6,597,520

SUMMARY OF THE INVENTION

An aspect of the present invention provides an optical element that is made of a transparent medium that is rotationally symmetric relative to the central axis with a refractive index greater than 1, wherein the transparent medium has a first transmissive surface arranged at the outermost periphery relative to the central axis, a first reflective surface arranged at the side of the central axis relative to the first transmissive surface, a second reflective surface arranged at the side opposite to the image plane relative to the first reflective surface and a second transmissive surface arranged at the image plane side relative to the second reflective surface, the flux of light entering the transparent medium goes into it by way of the first transmissive surface so as to be reflected to the side opposite to the image plane by the first reflective surface and then to the image plane side by the second reflective surface to form an optical path before going out from the transparent medium at the image plane side by way of the second transmissive surface in the order of forward ray tracing and the optical path is formed only at a side relative to the central axis.

Preferably, the transparent medium has a view angle of about 90° at a side in a cross section including the central axis thereof and as viewed from a direction orthogonal relative to the central axis, and the optical path is formed a substantially Z-shaped optical path.

Preferably, an optical element as defined above satisfies the condition of $$0.01 < \beta\omega < 0.5 \quad (1),$$

where $\beta\omega$ is the angular magnification of meridional cross section of the optical element.

Preferably, the meridional cross section of the second transmissive surface represents negative power and that the optical element satisfies the condition of $$-10 < P2 < Pm < -1 \quad (2),$$

where P2 is the power of the second transmissive surface and Pm is the power of the entire optical system at the meridional cross section of the central principal ray of light.

Preferably, an optical element as defined above is formed by a transparent medium representing a refractive index not smaller than 1.5.

Preferably, at least either the first reflective surface and the second reflective surface has a total reflection effect.

Preferably, at least either the first reflective surface is formed by an extended rotary free curved surface formed by rotating a line segment of arbitrary shape having no plane of symmetry around the central axis.

Preferably, at least one of the surfaces that the transparent medium has is formed by an extended rotary free curved surface formed by rotating a line segment of arbitrary shape including one or more than one odd-number-th degree terms.

Another aspect of the present invention provides an optical system having an optical element according to the present invention, wherein it includes a front group, a back group arranged at the side of the image plane relative to the front group and an aperture arranged between the front group and the back group and that the optical element is arranged in the front group to form an image of an object arranged so as to surround the central axis or project an image of the object in a radial direction from the central axis.

Preferably, an optical system as defined above forms an image of an annular object around the central axis in a plane orthogonal relative to the central axis.

Preferably, the first reflective surface and the second reflective surface are arranged with their concave surfaces directed to the aperture.

Preferably, the second transmissive surface is arranged with its concave surface directed to the aperture.

Preferably, an optical system as defined above does not form any intermediate image on the optical path.

Preferably, the optical element is arranged at the side opposite to the image plane relative to the aperture.

Preferably, the optical element has a direct view optical path for observing the direct front of the optical element and a side view optical path for observing the direction that is orthogonal relative to the central axis and forms an image of the direct view optical path and an image of the side view optical path on the same plane.

Preferably, an optical system as defined above satisfies the condition of $$D/Dr<10 \tag{3}$$

where D is the external dimension of the optical element and Dr is the external dimension of the image.

Preferably, an optical system as defined above satisfies the condition of $$D<20 \text{ mm} \tag{4}$$

where D is the external dimension of the optical element.

Another aspect of the present invention provides an endoscope formed by using an optical system as defined above.

Another aspect of the present invention provides an optical element, wherein it is made of a transparent medium rotationally symmetric relative to the central axis with a refractive index greater than 1, that the transparent medium has a first transmissive surface arranged at the outermost periphery relative to the central axis, a first reflective surface arranged at the side of the central axis relative to the first transmissive surface, a second reflective surface arranged at the side opposite to the image plane relative to the first reflective surface, a third reflective surface arranged at the side opposite to the image plane relative to the second reflective surface and a second transmissive surface arranged at the image plane side relative to the third reflective surface, that the flux of light entering the transparent medium goes into it by way of the first transmissive surface so as to be reflected to the image plane side by the first reflective surface, then to the side opposite to the image plane by the second reflective surface and then to the image plane side by the third reflective surface to form an optical path before going out from the transparent medium at the image plane side by way of the second transmissive surface in the order of forward ray tracing and that the optical path is formed only at a side relative to the central axis.

Preferably, the transparent medium has a view angle of about 90° at a side in a cross section including the central axis thereof and as viewed from a direction orthogonal relative to the central axis and the optical path is formed a substantially w-shaped optical path.

Preferably, an optical element as defined above satisfies the condition of $$0.01<\beta\omega<0.5 \tag{1}$$

where βω is the angular magnification of meridional cross section of the optical element.

Preferably, the meridional cross section of the second transmissive surface represents negative power and that the optical element satisfies the condition of $$-10<P2<Pm<-1 \tag{2}$$

where P2 is the power of the second transmissive surface and Pm is the power of the entire optical system at the meridional cross section of the central principal ray of light.

Preferably, an optical element as defined above is formed by a transparent medium having a refractive index not smaller than 1.5.

Preferably, at least one of the first reflective surface, the second reflective surface and the third reflective surface has a total reflection effect.

Preferably, at least one of the first reflective surface, the second reflective surface and the third reflective surface is formed by an extended rotary free curved surface formed by rotating a line segment of arbitrary shape having no plane of symmetry around the central axis.

Preferably, at least one of the surfaces that the transparent medium has is formed by an extended rotary free curved surface formed by rotating a line segment of arbitrary shape including one or more than one odd-number-th degree terms.

Another aspect of the present invention provides an optical system having an optical element according to the present invention, wherein it includes a front group, a back group arranged at the side of the image plane relative to the front group and an aperture arranged between the front group and the back group and that the optical element is arranged in the front group to form an image of an object arranged so as to surround the central axis or project an image of the object in a radial direction from the central axis.

Preferably, an optical system as defined above forms an image of an annular object around the central axis in a plane orthogonal relative to the central axis.

Preferably, the first reflective surface, the second reflective surface and the third reflective surface are arranged with their concave surfaces directed to the aperture.

Preferably, the second transmissive surface is arranged with its concave surface directed to the aperture.

Preferably, an optical system as defined above does not form any intermediate image on the optical path.

Preferably, the optical element is arranged at the side opposite to the image plane relative to the aperture.

Preferably, an optical system as defined above satisfies the condition of $$D/Dr<10 \tag{3}$$

where D is the external dimension of the optical element and Dr is the external dimension of the image.

Preferably, an optical system as defined above satisfies the condition of $$D<20 \text{ mm} \tag{4}$$

where D is the external dimension of the optical element.

Another aspect of the present invention provides an endoscope formed by using an optical system as defined above.

Thus, the present invention provides a compact optical system having a simple configuration and excellent resolving power for which aberrations are corrected satisfactorily and that can observe or project an image in different directions.

DETAILED DESCRIPTION OF PREFERRED EMBODIMENTS

Now, an optical element and an optical system including such an optical element according to the present invention will be described below based on Examples 1 through 3.

Figure 3:
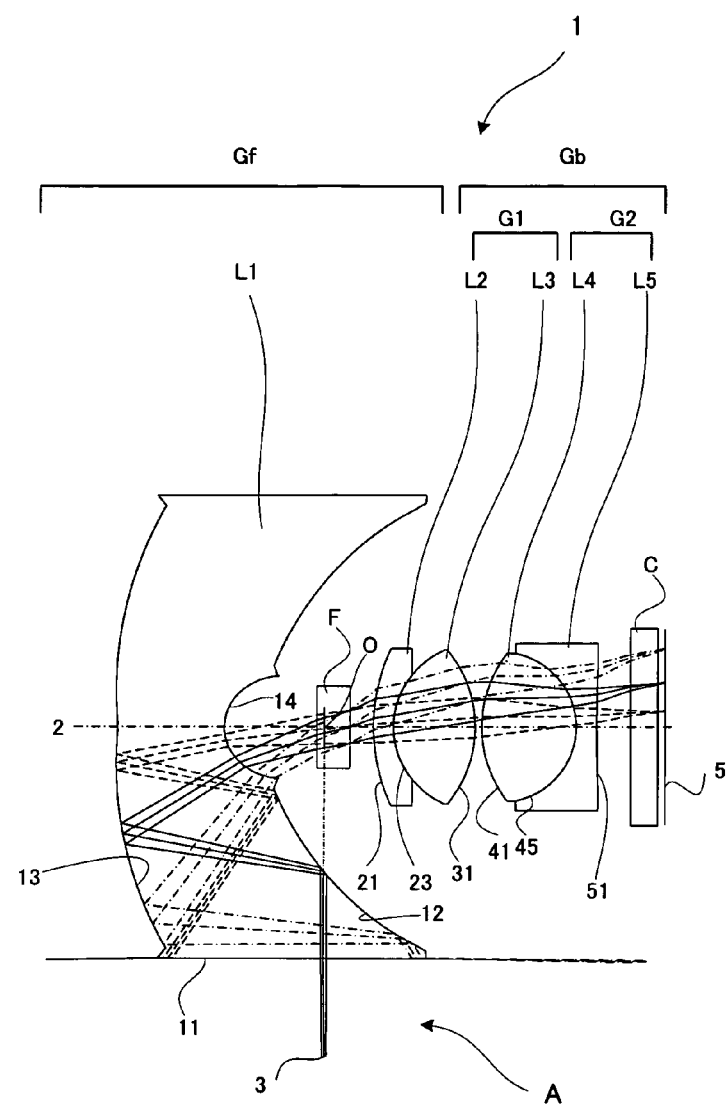
FIG. 3 is a schematic cross-sectional view of the optical system of Example 1 of the present invention taken along the central axis thereof.

FIG. 3 is a schematic cross sectional view of the optical system 1 of Example 1 of the present invention, which will be described in greater detail hereinafter, taken along the central axis (axis of rotational symmetry) 2 thereof. Note that, while the optical system is described below in terms of image formation optical system, it is also applicable to a projection optical system by using the optical path reversely.

The optical system 1 of Example 1 includes a front group Gf that is rotationally symmetric relative to central axis 2 and having negative power, an aperture S and a back group Gb having positive power and can form or project an image without forming an intermediate image on any optical path. The parallel flat plate near the image plane 5 is typically a cover glass C for the imaging element.

Therefore, the embodiment of the present invention provides a compact and inexpensive optical element that has a simple configuration and can form an omni-directional image in a direction substantially orthogonal to the central axis on a single imaging element with little image distortions and high resolving power to represent an excellent F-θ characteristic, an optical system having such an optical element and also an endoscope formed by using such an optical system.

Thus, the embodiment of the present invention provides a compact optical system having a simple configuration and excellent resolving power for which aberrations are corrected satisfactorily and that can observe or project an image in different directions.

The optical system becomes of a so-called retro-focus type when the front group Gf is made negative and the back group Gb is made positive. Such an arrangement is effective particularly when a wide view angle needs to be secured.

An optical element according to the present invention has a view angle of about 180° at a side in a cross section including the central axis 2 thereof and as viewed from a direction orthogonal relative to the central axis 2 and is made of a transparent medium L1 rotationally symmetric relative to the central axis 2 with a refractive index greater than 1, that the transparent medium L1 has a first transmissive surface 11 arranged at the outermost periphery relative to the central axis 2, a first reflective surface 12 arranged at the side of the central axis relative to the first transmissive surface, a second reflective surface 13 arranged at the side opposite to the image plane 5 relative to the first reflective surface 12 and a second transmissive surface 14 arranged at the side of the image plane 5 relative to the second reflective surface 13 and the flux of light entering the transparent medium L1 goes into the transparent medium L1 by way of the first transmissive surface 11 so as to be reflected to the side opposite to the image plane 5 by the first reflective surface 12 and then to the side of the image plane 5 by the second reflective surface 13 to form a substantially Z-shaped optical path A before going out from the transparent medium L1 at the side of the image plane 5 by way of the second transmissive surface 14 in the order of forward ray tracing, the optical path A being formed only at a side of the central axis 2.

With the above-described arrangement, the angle of incidence relative to the first reflective surface 12 and the second reflective surface 13 of the optical path A can be made relatively small while a large view angle of about 90° can be secured at a side, the occurrence of eccentric aberration occurred at the reflective surface can be minimized. Additionally, the optical path does not cross the central axis 2 in the optical element to make it possible to reduce the thickness of the optical element as the optical path A is arranged only at a side of the central axis.

Preferably, an optical element according to the present invention satisfies the condition of $$0.01 < \beta\omega < 0.5 \quad (1),$$

where $\beta\omega$ is the angular magnification of meridional cross section of the optical element. This conditional formula indicates the angular reduction magnification at a meridional cross section. The load on the optical element becomes too large when the angular magnification falls below the lower limit of the conditional formula (1) so that the optical element may become abnormally large and/or expensive glass having an abnormally high refractive index may be required. The view angle reducing effect of the optical element is lost when the angular magnification exceeds the upper limit of the conditional formula (1) so that the view angle of the flux of light entering the back group may become very wide to increase the load on the back group.

Still preferably, an optical element according to the present invention satisfies the condition of $$0.02 < \beta\omega < 0.2 \quad (1\text{-}1).$$

Preferably, an optical element according to the present invention satisfies the condition of $$-10 < P2/Pm < -1 \quad (2),$$

where P2 is the power of the second transmissive surface 14 and Pm is the power of the entire optical system at the meridional cross section of the central principal ray of light.

The conditional formula (2) above indicates the ratio that the second transmissive surface 14 takes in the total power. The negative power of the second transmissive surface 14 becomes large to make it possible to reduce the angular magnification when the above ratio falls below the lower limit of the conditional formula (2), although the comatic aberration and the astigmatism that arise on this surface becomes too large for the other surfaces to correct them. The negative power of the second transmissive surface 14 becomes too small to make the angular magnification of the meridional cross section large as in the case of the conditional formula (1) when the above ratio exceeds the upper limit of the conditional formula (2). Then, the load of the back group becomes too large to make the optical system inevitably bulky.

It is possible to reduce the aberrations when a medium having a refractive index not smaller than 1.5 is employed for the optical element and the surfaces having a reflective effect are formed by using internal reflective surfaces if compared with an arrangement where the surfaces having a reflective effect are formed by reflective surfaces. With such an arrangement, it is possible to form a compact and high-resolution optical system and, at the same time, integrate two reflective surfaces to a great advantage from the viewpoint of assembly and adjustment.

Preferably, a medium representing a refractive index not smaller than 1.7 is used for the optical element. The curvature of an internal reflective surface can be reduced (and hence the radius of curvature thereof can be increased) by using a medium having a high refractive index so that, particularly when forming an eccentric optical system as in the case of the present invention, the occurrence of eccentric aberration can be minimized to improve the resolution.

It is more preferable to use medium having a refractive index not smaller than 1.8 for the optical element. Then, the critical angle becomes equal to 33° to make it possible to form the first reflective surface as a total reflective surface. Then, no reflection coating is required to a great advantage from the viewpoint of processing and prevention of loss of quantity of light.

No reflective membrane is required when at least either the first reflective surface 12 or the second reflective surface 13 is made to have a total reflection effect. Then, an optical system can be manufactured with ease and the reflectance becomes equal to 100% to make it possible to pick up a bright image.

Additionally, the distortions at and near the view angle can be corrected when at least either the first reflective surface 12 and the second reflective surface 13 is formed by an extended rotary free curved surface formed by rotating a line segment of arbitrary shape having no plane of symmetry around the central axis 2.

Still additionally, an optical element according to the present invention can be made to have a shape that is vertically asymmetric relative to the center of the view angle to make it advantageous for correcting aberrations when at least one of the surfaces that the transparent medium L1 has is formed by an extended rotary free curved surface formed by rotating a line segment of arbitrary shape including one or more than one odd-number-th degree terms around the central axis 2.

Both of the two reflective surfaces having a reflection effect are so arranged that the concave surfaces thereof are directed to the aperture S. Then, as a result, the reflective surfaces represent a negative-positive power arrangement to make the power arrangement of the reflective surfaces of the optical element itself a retro-focus type so that it can take a wide view angle with ease and comatic aberration hardly arises there.

Preferably, the second transmissive surface is a surface having strong negative power with its concave surface directed to the aperture side. The view angle of the ray of light entering the back group can be reduced to by turn reduce the load of correcting the aberrations of the back group. It is possible to realize a compact optical system with a small number of constituent surfaces by reducing the view angle of the ray of light passing through the surface and going out from the optical element.

Additionally, the front group and the back group are made well balanced to produce a favorable effect for downsizing and simplifying the optical system by arranging the optical element close to the object relative to the aperture. It is hardly possible to achieve a large angular magnification and the load of the other lenses is raised when the optical element is arranged near the aperture because the central ray of light of a meridional cross section and a ray of light having a large view angle are found close to each other in the vicinity of the aperture. Additionally, it is not possible to provide a wide view angle for the front group located at the side of the object relative to the aperture when the optical element is arranged at the image side of the aperture.

Figure 6:
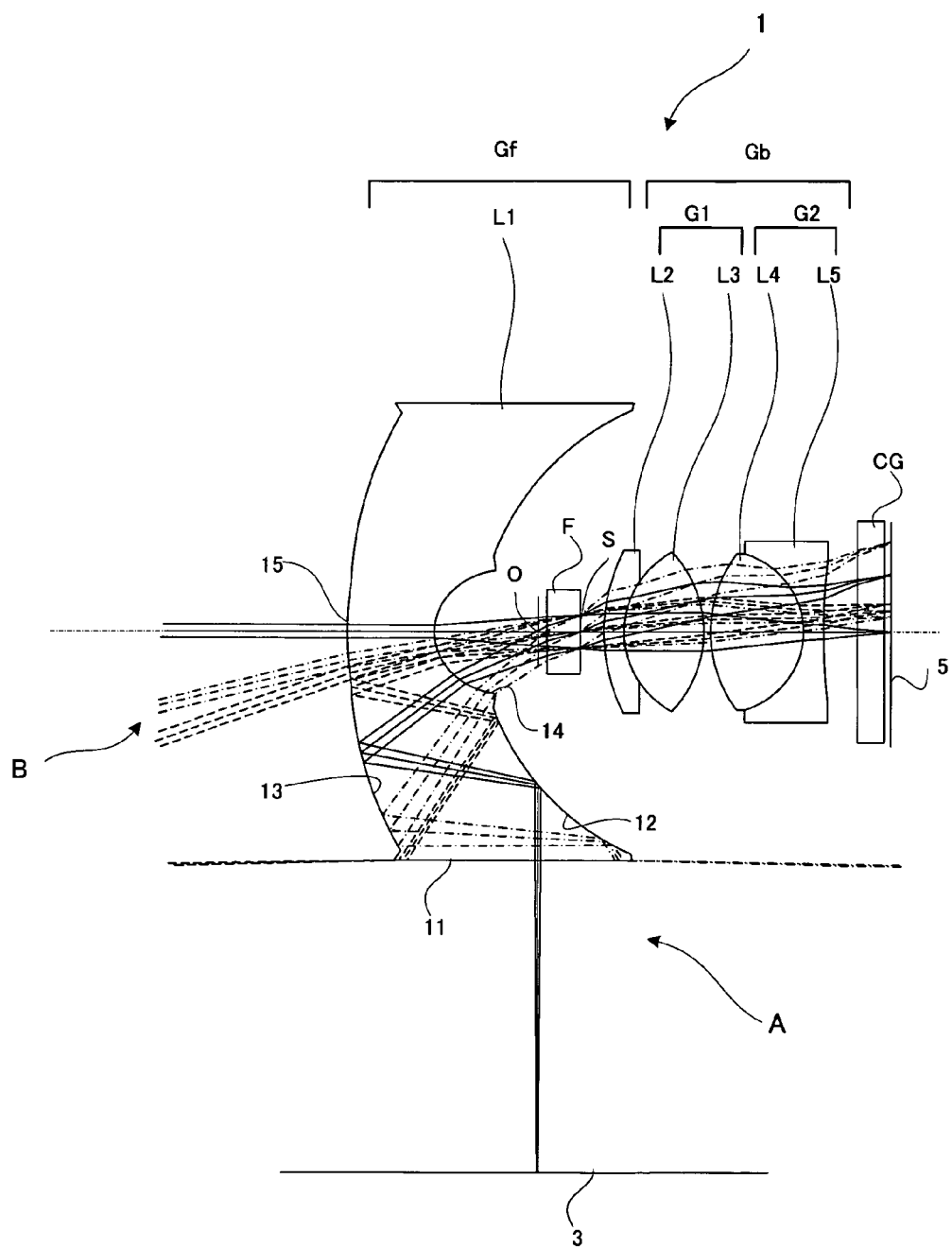
FIG. 6 is a schematic cross-sectional view of the optical system of Example 2 of the present invention taken along the central axis thereof.

FIG. 6 is a schematic cross-sectional view of the optical system 1 of Example 2 of the present invention, which will be described in greater detail hereinafter, taken along the central axis (axis of rotational symmetry) 2 thereof. The optical element of this example has a side view optical path for obtaining a lateral image as viewed from the central axis like the one described above for Example 1 and additionally a direct view optical path for obtaining a front view along the central axis of the optical system passing through the center of the optical element. When the optical element is formed so as to allow it to have two optical paths including a side view optical path A and a direct view optical path B, the number of optical elements of the optical system can be reduced to make it possible to downsize the optical system because the other optical elements can share part of the optical system. Additionally, it is possible to focus the two images simultaneously by means of a single imaging element to pick up clear images by projecting the images of the two optical paths on the same plane.

Still preferably, the optical system satisfies the condition of $$D/Dr<10 \tag{3},$$

where D is the external dimension of the optical element and Dr is the external dimension of the image.

The outer diameter of the optical system becomes large relative to the imaging element when the above ratio exceeds the upper limit of the conditional formula (3). The size of an imaging element is determined to a certain extent as a function of its price and its noise. For example, it will be impossible to form a compact optical system as a whole when a ⅓ or ¼-inch high-resolution imaging element that can be obtained at relatively low cost is employed and the upper limit of the conditional formula (3) is exceeded.

More preferably, the optical system satisfies the condition of $$D/Dr<5 \tag{3-1}.$$

Still preferably, the outer diameter D of the optical element satisfies the condition of $$D<20 \text{ mm} \tag{4}.$$

In particular, when the optical element is used for an image pickup system of an endoscope, the condition of the conditional formula (4) is preferably satisfied to reduce the load on the part of the subject of examination.

More preferably, the outer diameter D of the optical element satisfies the condition of $$D<10 \text{ mm} \tag{4-1}.$$

Now, Examples 1 through 3 of optical system according to the present invention will be described below. The parameters of the optical systems of these examples will be described hereinafter.

Figure 1:
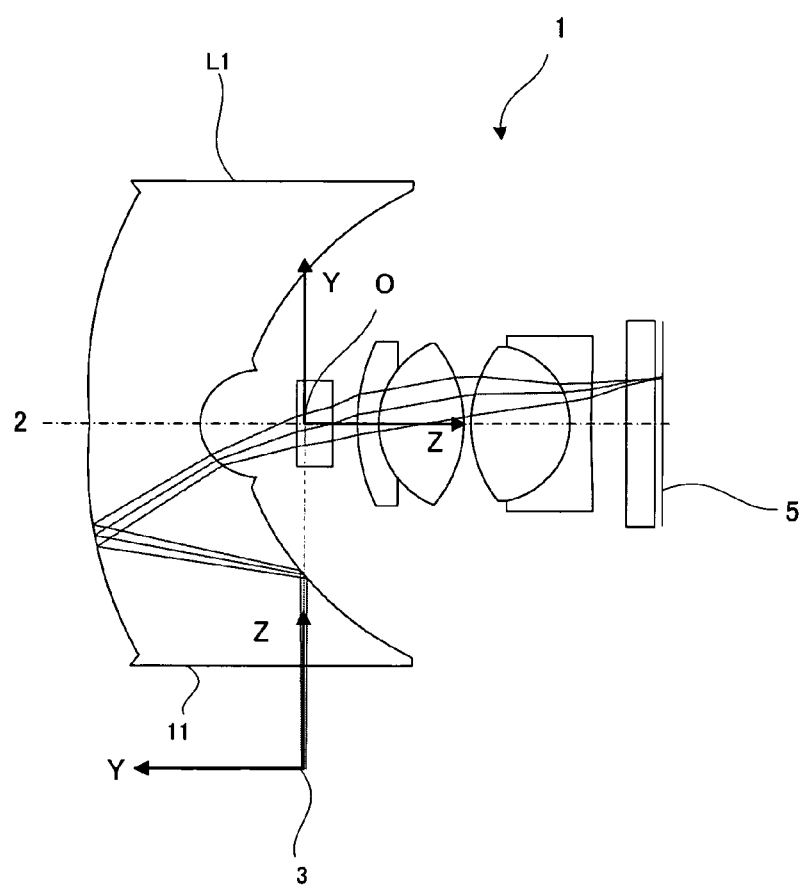
FIG. 1 is a schematic illustration of the coordinate system of the optical systems of Examples 1 through 3 according to the present invention.

As coordinate system in forward ray tracing, for instance, the point of intersection of a prolonged line of the central principal ray of light proceeding from the object surface 3 toward the first surface and the central axis 2 is taken as origin O of eccentric optical surface and the direction orthogonal to the central axis 2 and of moving toward the side opposite to the object surface 3 as viewed from the central axis 2 is taken as a Y-axis positive direction as illustrated in FIG. 1, whereas the surface plane of the sheet of FIG. 1 is taken as a Y-Z plane. Then, the direction of moving toward the image plane 5 in FIG. 1 is taken as a Z-axis positive direction and the axis that constitutes a right hand orthogonal coordinate system with the Y-axis and the Z-axis is taken as an X-axis positive direction.

As for the eccentric surface, the eccentricity from the origin O of the above optical system 1 that is used for defining the coordinate system that by turn defines the surface (as expressed by X, Y and Z respectively in the X-axis direction, the Y-axis direction and the Z-axis direction) and the angles of inclination of the planes extending respectively through the X-axis, the Y-axis and the Z-axis in the coordinate system that is defined by using the origin O of the optical system 1 ($\alpha$, $\beta$ and $\gamma$ (°) respectively) are given. Note that $\alpha$ and $\beta$ are taken as positive respectively in the counterclockwise directions relative to the positive direction of the X-axis and that of the Y-axis and $\gamma$ is taken as positive in the clockwise direction relative to the position direction of the Z-axis. Also note that each of the planes is rotated around the central axis thereof by $\alpha$, $\beta$ and $\gamma$ in such a way that the coordinate system that defines the planes is rotated firstly counterclockwise by $\alpha$ around the X-axis of the coordinate system that is defined by using the origin of the optical system and then the coordinate system obtained by rotating the initial coordinate system is rotated counterclockwise by $\beta$ around the Y-axis thereof. Then, finally, the coordinate system obtained by rotating the second coordinate system is rotated clockwise by $\gamma$ around the Z-axis thereof.

When a specific plane and the subsequent plane of the optical acting planes that the optical system of each of the examples includes form a coaxial optical system, the plane gap is given. Otherwise, the radius of curvature of each plane, the refractive index of the medium and the Abbe number are given according to the common practice.

All the terms relating to aspheric planes that are not described in the data on the constituent parameters that will be described hereinafter are equal to 0. The refractive index and the Abbe number relative to d-lines (wavelength: 587.56 nm) are given. The unit of length is mm. The eccentricity of each plane is expressed by the eccentricity from the reference plane as described above.

An aspheric plane is a rotationally symmetric defined by the formula represented below.

$$Z=(Y^2/R)/[1+\{1-(1+k)Y^2/R^2\}^{1/2}]+aY^4+bY^6+cY^8+dY^{10}+\ldots \tag{a}$$

provided that Z is selected as an axis and Y denotes a direction perpendicular to the axis. In the above formula, R is the near-axis radius of curvature, k is the conic constant and a, b, c, d, . . . are respectively the aspheric surface coefficients of the fourth degree, the sixth degree, the eighth degree, the tenth degree and so on. The Z-axis of the above defining formula operates as the axis of a rotationally symmetric aspheric surface.

An extended rotary free curved surface is a rotationally symmetric surface given by the following definition.

Figure 2:
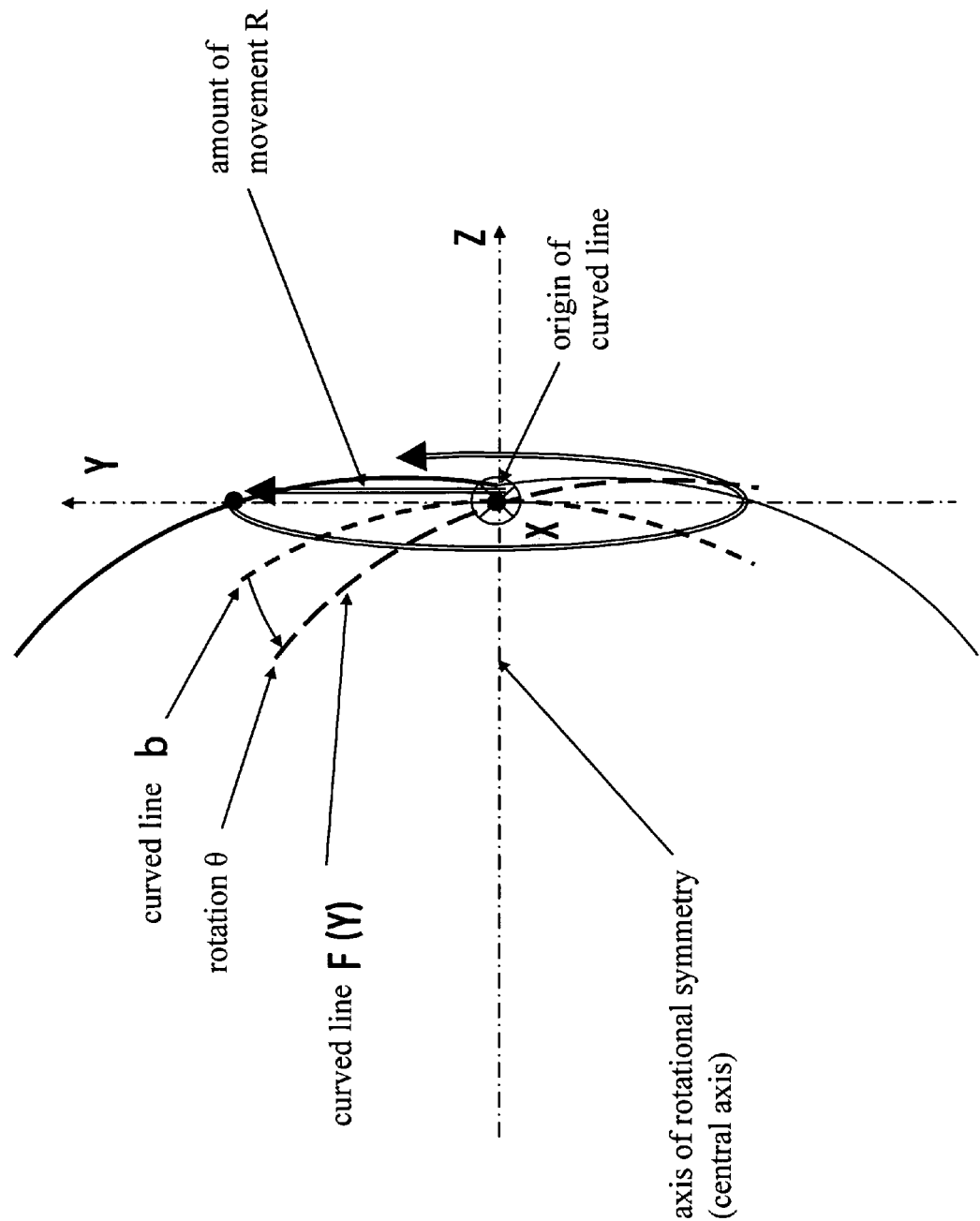
FIG. 2 is a schematic illustration of the principle of extended rotary free curved surfaces.

Firstly, a curved line (b) that passes through the origin on the Y-Z coordinate plane as illustrated in FIG. 2 is defined.

$$Z=(Y^2/RY)/[1+\{1-(C_1+1)Y^2/RY^2\}^{1/2}]+C_2Y+C_3Y^2+C_4Y^3+C_5Y^4+C_6Y^5+C_7Y^6+\ldots+C_{21}Y^{20}+\ldots+C_{n+1}Y^n+\ldots \tag{b}$$

Then, curbed line F(Y) is defined by rotating the curbed line (b) by angle $\theta$(°), which is positive when it is rotated counterclockwise, facing in the positive direction of the X-axis. The curved line F(Y) also passes through the origin on the Y-Z coordinate plane.

The curved line F(Y) is translated in the direction of the positive direction of the Y-axis by distance R (in the negative direction of the Y-axis when it represents a negative value) and subsequently the translated curved line is rotated around the Z-axis to form a rotationally symmetric surface, which is an extended rotary free curved surface.

Then, as a result, the extended rotary free curved surface produces a free curved surface (free curved line) in the Y-Z plane and a circle of radius |R| in the X-Y plane.

From the above definition, the Z-axis operates as the axis (the axis of rotational symmetry) of the extended rotary free curved surface.

In the above formula (b), RY is the radius of curvature of the sphere term in the Y-Z cross section, $C_1$ is the conic constant and $C_2$, $C_3$, $C_4$, $C_5$, . . . are respectively the aspheric coefficients of the first degree, the second degree, the third degree, the fourth degree and so on.

Note that a surface of circular cone whose central axis is parallel to the Z-axis is given as an extended rotary free curved surface with RY=∞, $C_1$, $C_2$, $C_3$, $C_4$, $C_5$, . . . =0, $\theta$=(the angle of inclination of the surface of circular cone) and R=(the radius of the bottom in the X-Z plane).

All the terms relating to aspheric planes that are not described in the data on the constituent parameters that will be described hereinafter are equal to 0. The refractive index and the Abbe number relative to d-lines (wavelength: 587.56 nm) are given. The unit of length is mm. The eccentricity of each plane is expressed by the eccentricity from the reference plane as described above.

Figure 4:
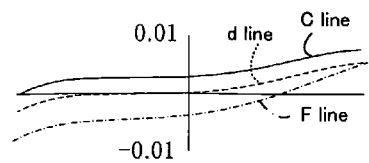
FIG. 4 is a schematic illustration of the transverse aberrations of the overall optical system of Example 1.
Figure 4:
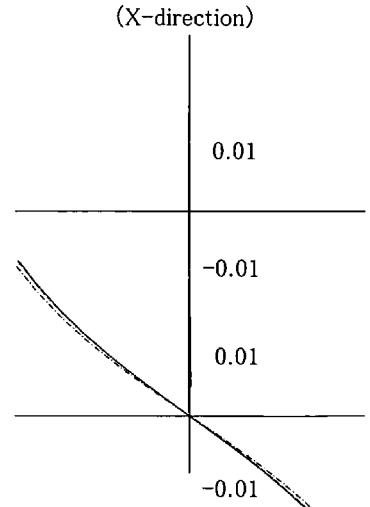
Figure 4:
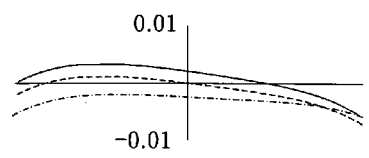
Figure 4:
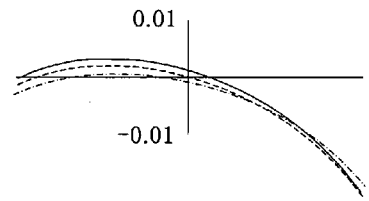
Figure 4:
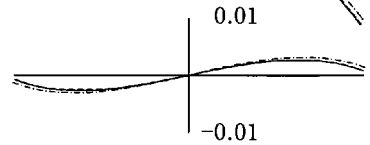
Figure 4:
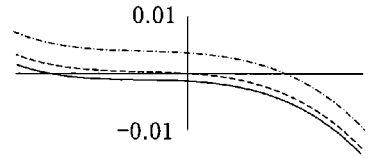
Figure 4:
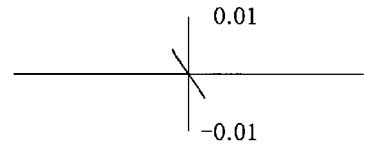
Figure 4:
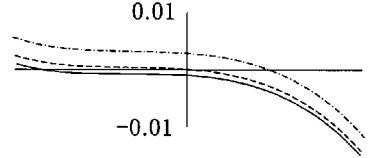
Figure 4:
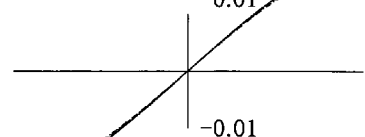
Figure 4:
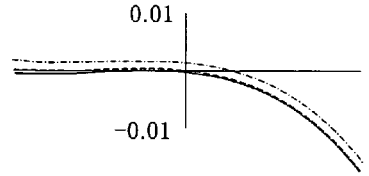
Figure 4:
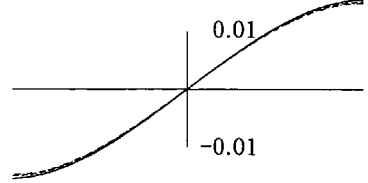
Figure 4:
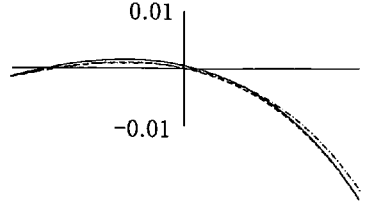
Figure 4:
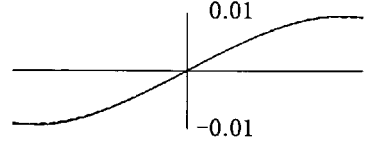
Figure 5:
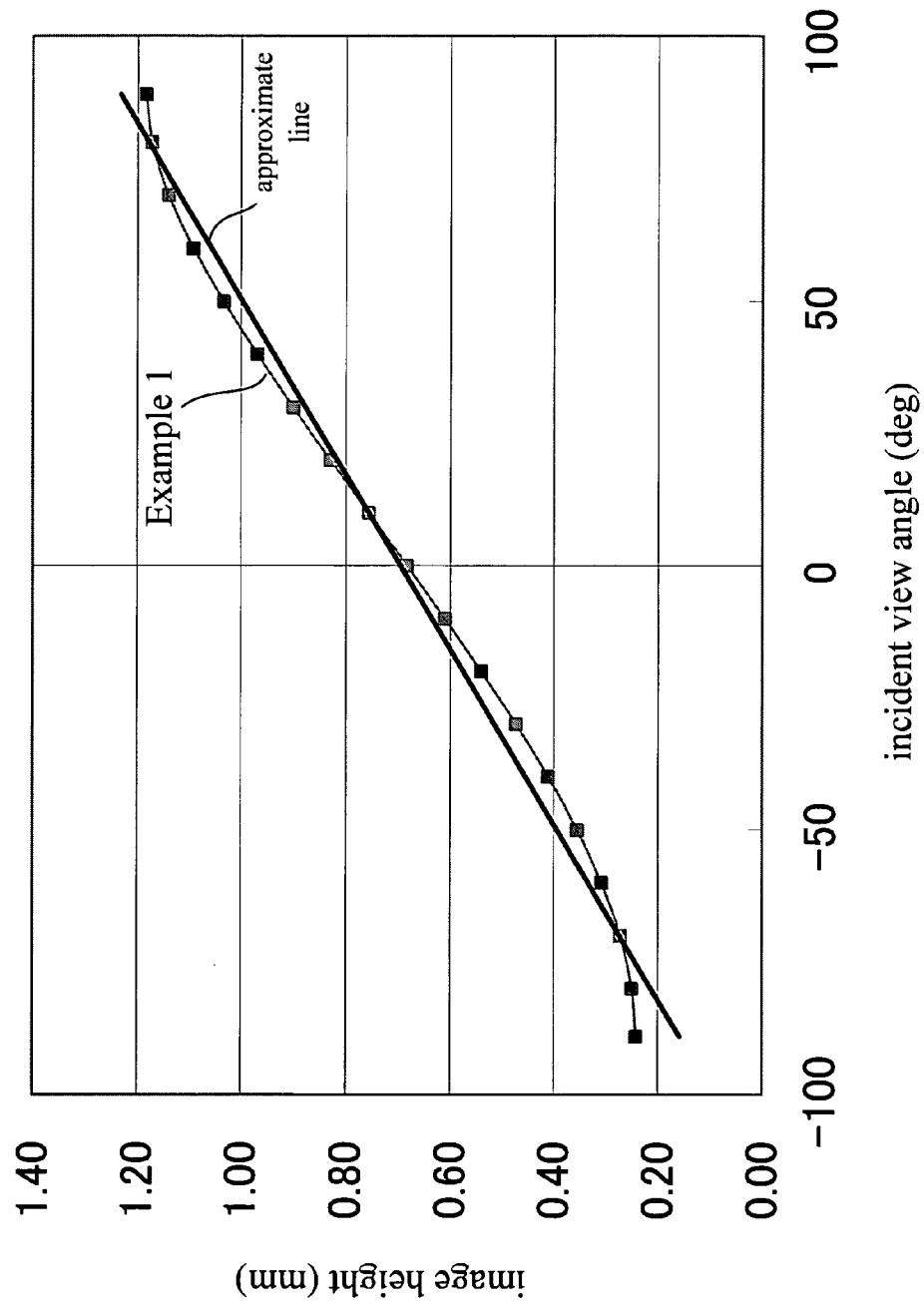
FIG. 5 is an F-θ graph of the overall optical system of Example 1.

FIG. 3 is a schematic cross-sectional view of the optical system 1 of Example 1 taken along the central axis 2 thereof. FIG. 4 is a schematic illustration of the transverse aberrations of the overall optical system of this example on the side view optical path thereof. FIG. 5 is a graph indicating the relationship between the view angle and the image height. In each of the views representing the transverse aberrations, each pair of angle values represented at the center indicates (the view angle in the horizontal direction, the view angle in the vertical direction). The transverse aberrations in the Y-direction (the meridional direction) and those in the X-direction (the sagittal direction) are also denoted. Note that a negative view angle in the horizontal direction denotes a clockwise angle observed by facing in the positive direction of the Y-axis, whereas a negative view angle in the vertical direction also denotes a clockwise angle observed by facing in the positive direction of the X-axis. This note is also applicable in the following similar descriptions.

In this example, none of the transmissive surfaces and the reflective surfaces of the transparent medium, that is concentric with and rotationally symmetric relative to the central axis 2 of the optical system 1 and has a refractive index greater than 1, is shared in the optical path and hence all the surfaces are different surfaces.

The optical system 1 includes a front group Gf that is rotationally symmetric relative to the central axis 2, a back group Gb that is also rotationally symmetric relative to the central axis 2 and an aperture S arranged between the front group Gf and the back group Gb so as to be coaxial with the central axis 2. The back group Gb includes a first group G1 and a second group G2.

The front group is formed by a transparent medium L1 that is rotationally symmetric relative to the central axis 2 and has a refractive index greater than 1. The transparent medium L1 has a cylindrical first transmissive surface 11 that is arranged at the external side vis-a-vis the object surface so as to be parallel to the central axis 2, a first reflective surface 12 that is formed by a toric surface in the inside of the transparent medium L1 at the side of the central axis 2 relative to the first transmissive surface 11 and has negative power, a second reflective surface 13 that is formed by a toric surface in the inside of the transparent medium L1 at the side opposite to the image plane 5 relative to the first reflective surface 12 and has positive power and a second transmissive surface 14 that is formed by an aspheric surface at the side of the image plane 5 relative to the second reflective surface 13 and has negative power.

The first group is formed by a cemented lens of a negative meniscus lens L2 with its concave surface directed to the side of the image plane 5 and a double convex positive lens L3 and has a third transmissive surface 21, a cementing surface 23 arranged at the side of the image plane 5 relative to the third transmissive surface 21 and a fourth transmissive surface 31 arranged at the side of the image plane 5 relative to the cementing surface 23.

The second group is formed by a cemented lens of a double convex positive lens L4 and a double concave negative lens L5 and has a fifth transmissive surface 41, a cementing surface 45 arranged at the side of the image plane 5 relative to the fifth transmissive surface 41 and a sixth transmissive surface 51 arranged at the side of the image plane 5 relative to the cementing surface 45.

The optical system 1 forms an optical path A. As for the optical path A, the flux of light entering it from the object surface 3 of the optical system 1 proceeds sequentially by way of the front group Gf and the back group Gb and forms an annular image off the central axis 2 of the image plane 5 extending perpendicularly relative to the central axis 2.

The flux of light entering the optical system 1 to proceed along the optical path A goes into the transparent medium L1 of the front group Gf by way of the first transmissive surface 11 so as to be reflected by the first reflective surface 12 to the side opposite to the image plane 5 and then by the second reflective surface 13 to the side of the image plane 5 to form a subsequently Z-shaped optical path before going out from the transparent medium L1 by way of the second transmissive surface 14.

Subsequently, the flux of light goes into the cemented lens of the negative meniscus lens L2 and the double convex positive lens L3 of the first group of the back group Gb at the opposite side relative to the central axis 2 by way of the aperture that is arranged between the front group Gf and the back group Gb coaxially with the central axis 2 to operate as a stop and the third transmissive surface 21 and goes out from the fourth transmissive surface 31 by way of the cementing surface 23. Then, it goes into the cemented lens of the double convex positive lens L4 and the double concave negative lens L5 of the second group by way of the fifth transmissive surface 41 and goes out from the sixth transmissive surface 51 by way of the cementing surface 45 to form an image at a radially predetermined position off the central axis 2 of the image plane 5.

The specifications of Example 1 are as follows.

| | |
|---|---|
| view angle | −89° to 89° |
| image size | ⌀0.48 to ⌀2.37 |
| F number | 3.97 |

Figure 7:
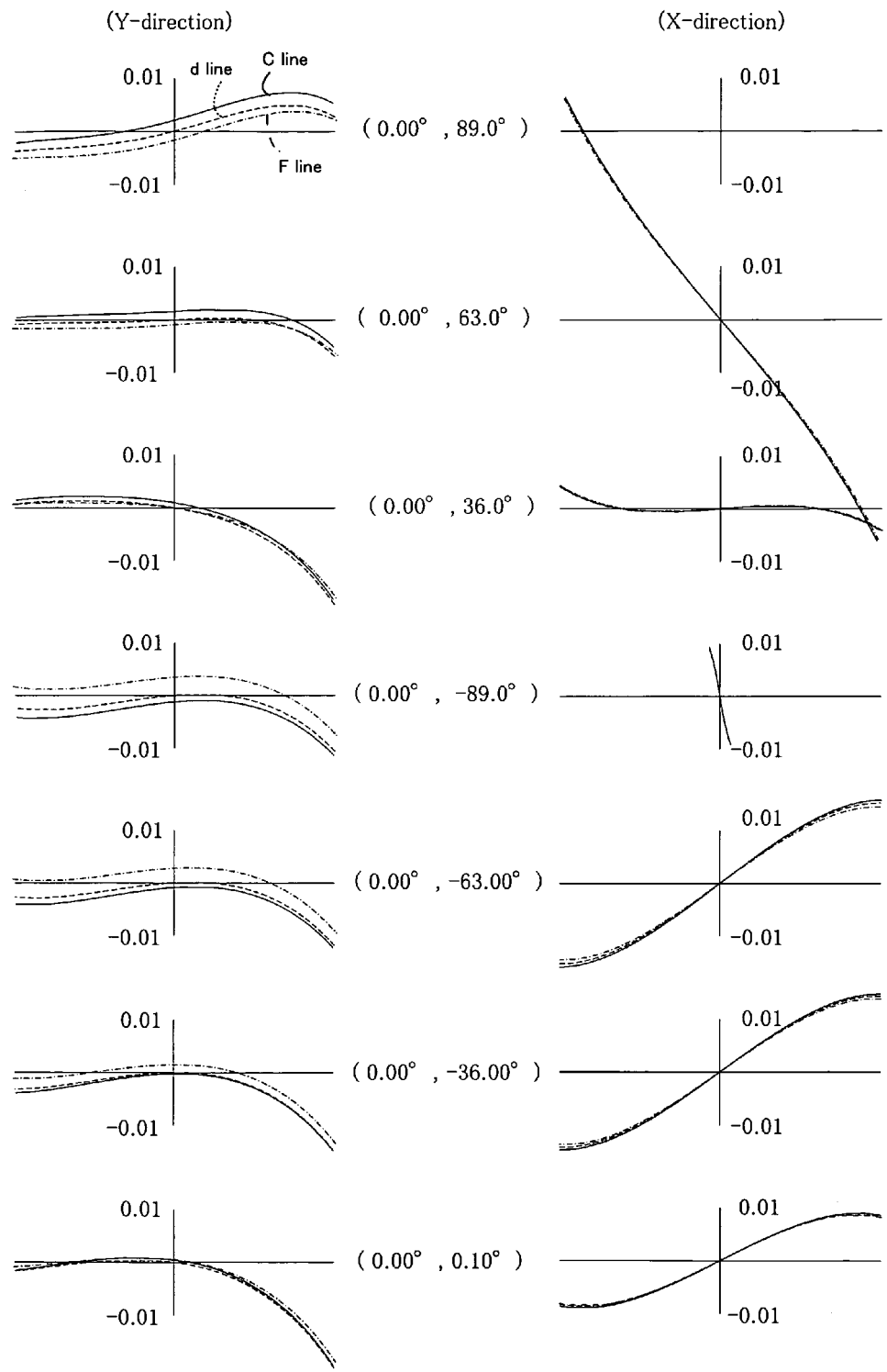
FIG. 7 is a schematic illustration of the transverse aberrations of the overall optical system of Example 2 on the side view optical path thereof.
Figure 8:
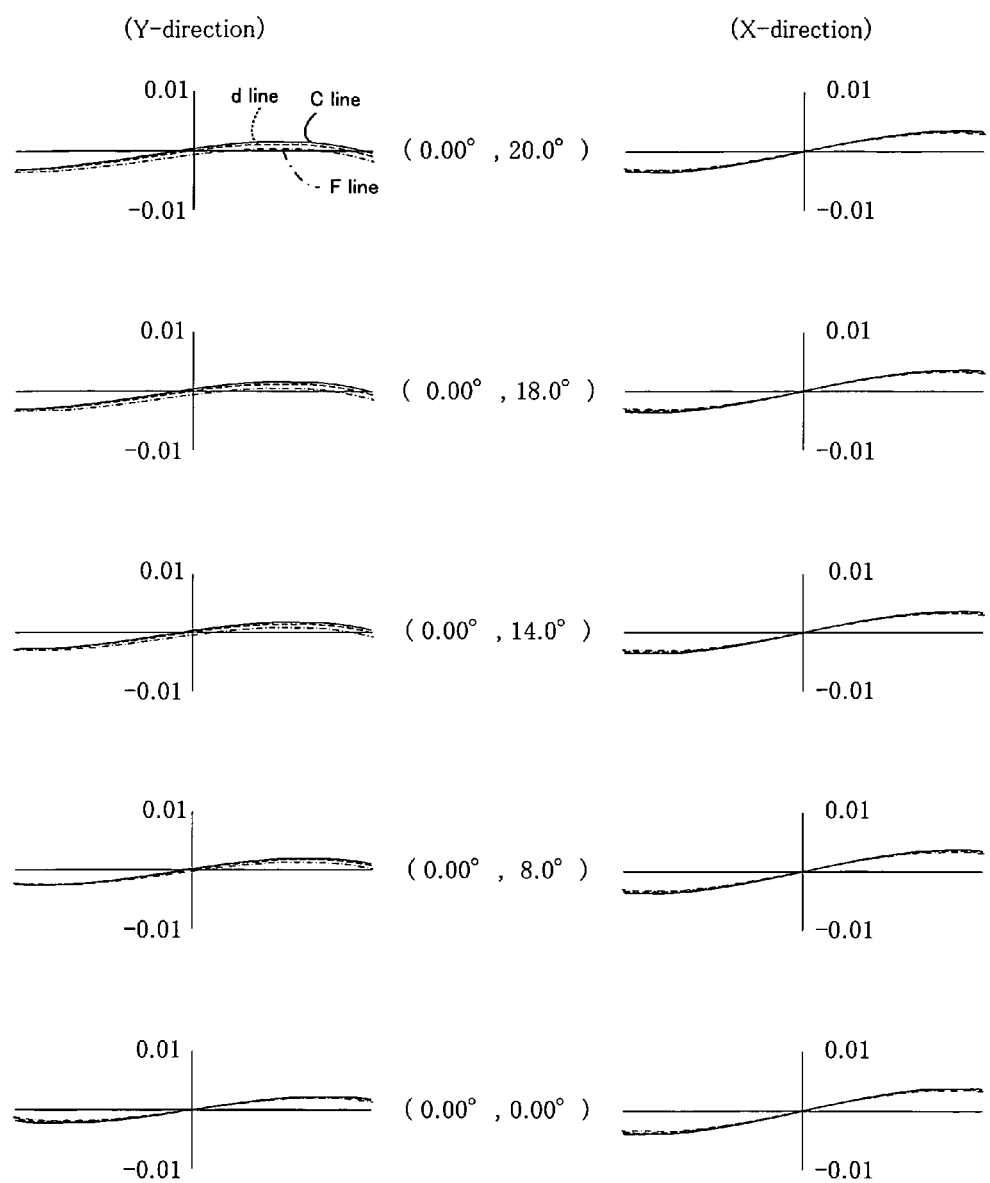
FIG. 8 is a schematic illustration of the transverse aberrations of the overall optical system of Example 2 on the direct view optical path thereof.
Figure 9:
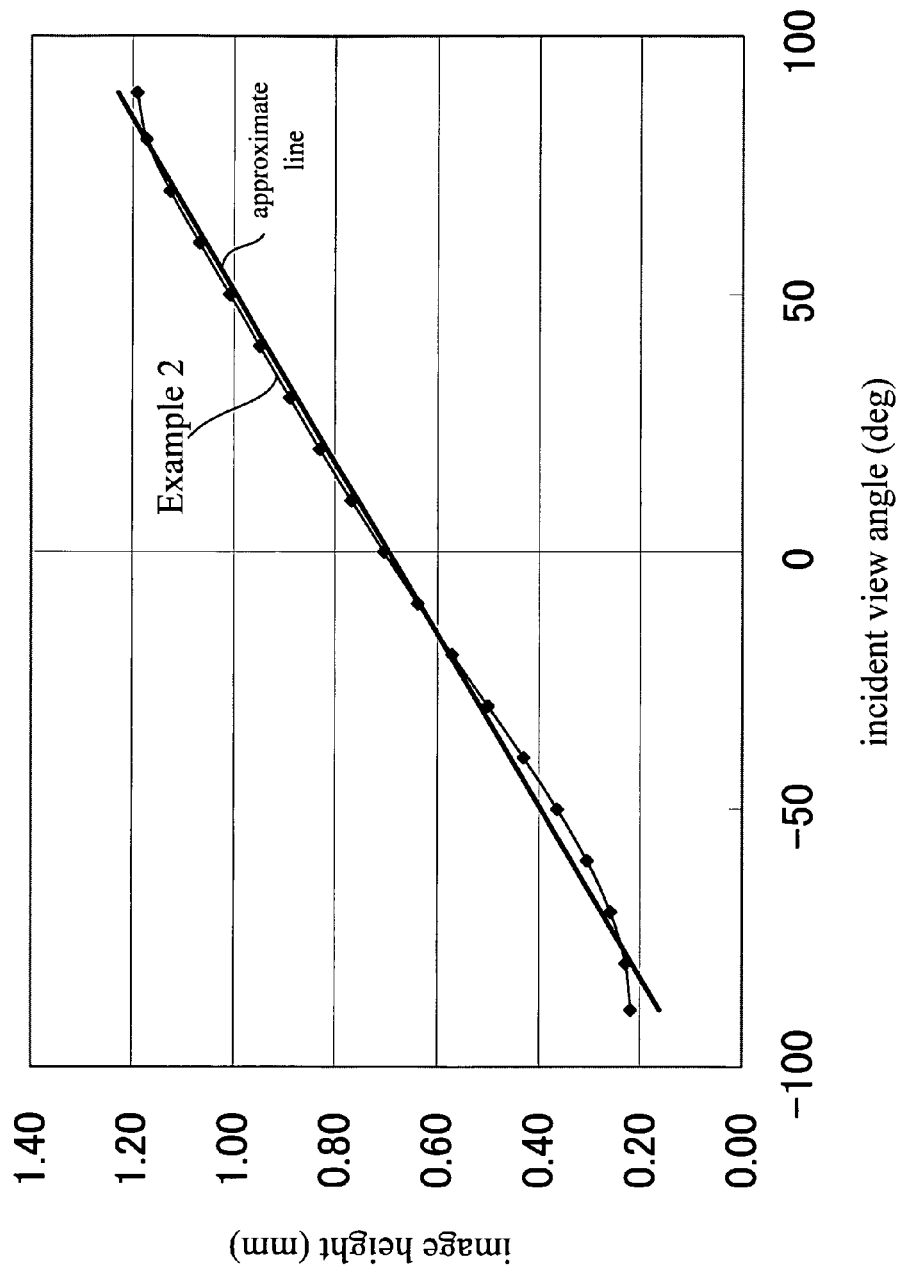
FIG. 9 is an F-θ graph of the overall optical system of Example 2.

FIG. 6 is a schematic cross-sectional view of the optical system 1 of Example 2 taken along the central axis 2 thereof. FIG. 7 is a schematic illustration of the transverse aberrations of the overall optical system of this example on the side view optical path thereof. FIG. 8 is a schematic illustration of the transverse aberrations of the overall optical system of this example on the direct view optical path thereof. FIG. 9 is a graph indicating the relationship between the view angle and the image height.

In this example, none of the transmissive surfaces and the reflective surfaces of the transparent medium, that is concentric with and rotationally symmetric relative to central axis 2 of the optical system 1 and has a refractive index greater than 1, is shared in the side view optical path and hence all the surfaces are different surfaces.

The optical system 1 includes a front group Gf that is rotationally symmetric relative to the central axis 2, a back group Gb that is also rotationally symmetric relative to the central axis 2 and an aperture S arranged between the front group Gf and the back group Gb so as to be coaxial with the central axis 2. The back group Gb includes a first group G1 and a second group G2.

The front group Gf is formed by a transparent medium L1 that is rotationally symmetric relative to the central axis 2 and has a refractive index greater than 1. It is an optical system for synthetically combining the side view optical path A and the direct view optical path B.

The transparent medium L1 has a cylindrical side view first transmissive surface 11 that is arranged at the external side vis-a-vis the side view object surface 3 so as to be parallel to the central axis 2, a side view first reflective surface 12 that is formed by a toric surface in the inside of the transparent medium L1 at the side of the central axis 2 relative to the side view first transmissive surface 11 and has negative power, a side view second reflective surface 13 that is formed by a toric surface in the inside of the transparent medium L1 at the side opposite to the image plane 5 relative to the side view first reflective surface 12 and has positive power and a side view second transmissive surface 14 that is formed by an aspheric surface at the side of the image plane 5 relative to the side view second reflective surface 13 and has negative power as well as a direct view third transmissive surface 15 formed by a spherical surface and has positive power and a direct view fourth transmissive surface 16 that is formed by an aspheric surface at the side of the image plane 5 relative to the direct view third transmissive surface 15 and has negative power. The side view second transmissive surface 14 and the direct view fourth transmissive surface 16 are the same surface.

The first group is formed by a cemented lens of a negative meniscus lens L2 with its concave surface directed to the side of the image plane 5 and a double convex positive lens L3 and has a third transmissive surface 21, a cementing surface 23 arranged at the side of the image plane 5 relative to the third transmissive surface 21 and a fourth transmissive surface 31 arranged at the side of the image plane 5 relative to the cementing surface 23.

The second group is formed by a cemented lens of a double convex positive lens L4 and a double concave negative lens L5 and has a fifth transmissive surface 41, a cementing surface 45 arranged at the side of the image plane 5 relative to the fifth transmissive surface 41 and a sixth transmissive surface 51 arranged at the side of the image plane 5 relative to the cementing surface 45.

The optical system 1 forms a side view optical path A and direct view optical path B. As for the side view optical path A, the flux of light entering it from the side view object surface 3 of the optical system 1 proceeds sequentially by way of the front group Gf and the back group Gb and forms an annular image off the central axis 2 of the image plane 5 extending perpendicularly relative to the central axis 2. As for the direct view optical path B, the flux of light entering it from the direct view object surface 4 near the central axis 2 of the optical system 1 proceeds sequentially by way of the front group Gf and the back group Gb and forms a circular image near the central axis 2 of the image plane 5 extending perpendicularly relative to the central axis 2.

The flux of light entering the optical system 1 from a lateral side thereof to proceed along the side view optical path A goes into the transparent medium L1 of the front group Gf by way of the side view first transmissive surface 11 so as to be reflected by the side view first reflective surface 12 to the side opposite to the image plane 5 and then by the side view second reflective surface 13 to the side of the image plane 5 to form a subsequently Z-shaped optical path before going out from the transparent medium L1 by way of the side view second transmissive surface 14.

Subsequently, the flux of light goes into the cemented lens of the negative meniscus lens L2 and the double convex positive lens L3 of the first group of the back group Gb at the opposite side relative to the central axis 2 by way of the aperture S that is arranged between the front group Gf and the back group Gb coaxially with the central axis 2 to operate as a stop and the common third transmissive surface 21 and goes out from the common fourth transmissive surface 31 by way of the cementing surface 23. Then, it goes into the cemented lens of the double convex positive lens L4 and the double concave negative lens L5 of the second group by way of the common fifth transmissive surface 41 and goes out from the common sixth transmissive surface 51 by way of the cementing surface 45 to form an image at a radially predetermined position off the central axis 2 of the image plane 5.

On the other hand, the flux of light entering the optical system 1 to proceed along the direct view optical path B goes into the transparent medium L1 of the front group Gf by way of the direct view first transmissive surface 15 and goes out from the transparent medium L1 by way of the direct view second transmissive surface 16 arranged at the side of the image plane 5 relative to the direct view first transmissive surface 15.

Subsequently, the flux of light goes into the cemented lens of the negative meniscus lens L2 and the double convex positive lens L3 of the first group of the back group Gb at the opposite side relative to the central axis 2 by way of the aperture S that is arranged between the front group Gf and the back group Gb coaxially with the central axis 2 to operate as a stop and the common third transmissive surface 21 and goes out from the common fourth transmissive surface 31 by way of the cementing surface 23. Then, it goes into the cemented lens of the double convex positive lens L4 and the double concave negative lens L5 of the second group by way of the common fifth transmissive surface 41 and goes out from the common sixth transmissive surface 51 by way of the cementing surface 45 to form an image on the central axis 2 of the image plane 5.

The specifications of Example 2 are as follows.

| view angle | (side view) | −89° to 89° |
|---|---|---|
| | (direct view) | 0° to 60° |
| image size | (side view) | ø0.87 to ø2.76 |
| | (direct view) | ø0.66 |
| F number | (side view) | 4.26 |
| | (direct view) | 4.24 |

Figure 10:
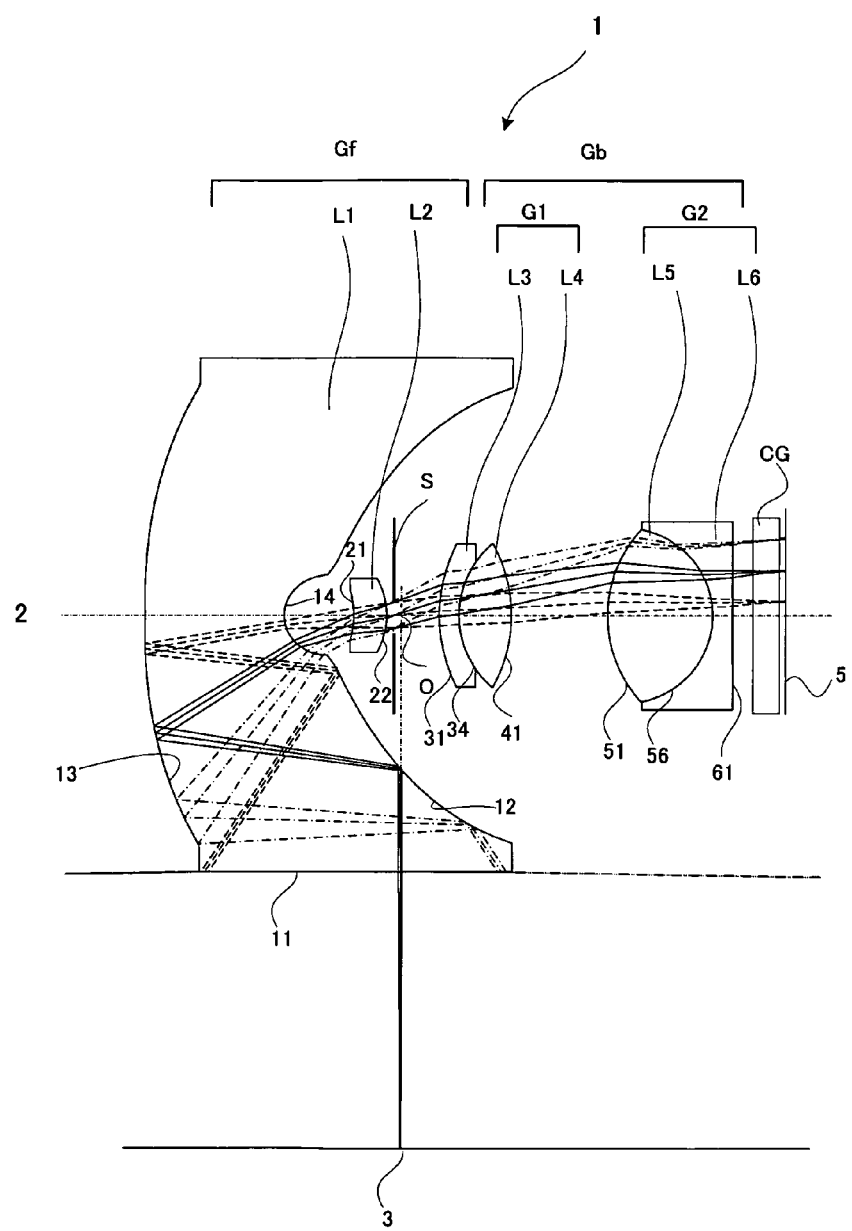
FIG. 10 is a schematic cross-sectional view of the optical system of Example 3 of the present invention taken along the central axis thereof.
Figure 11:
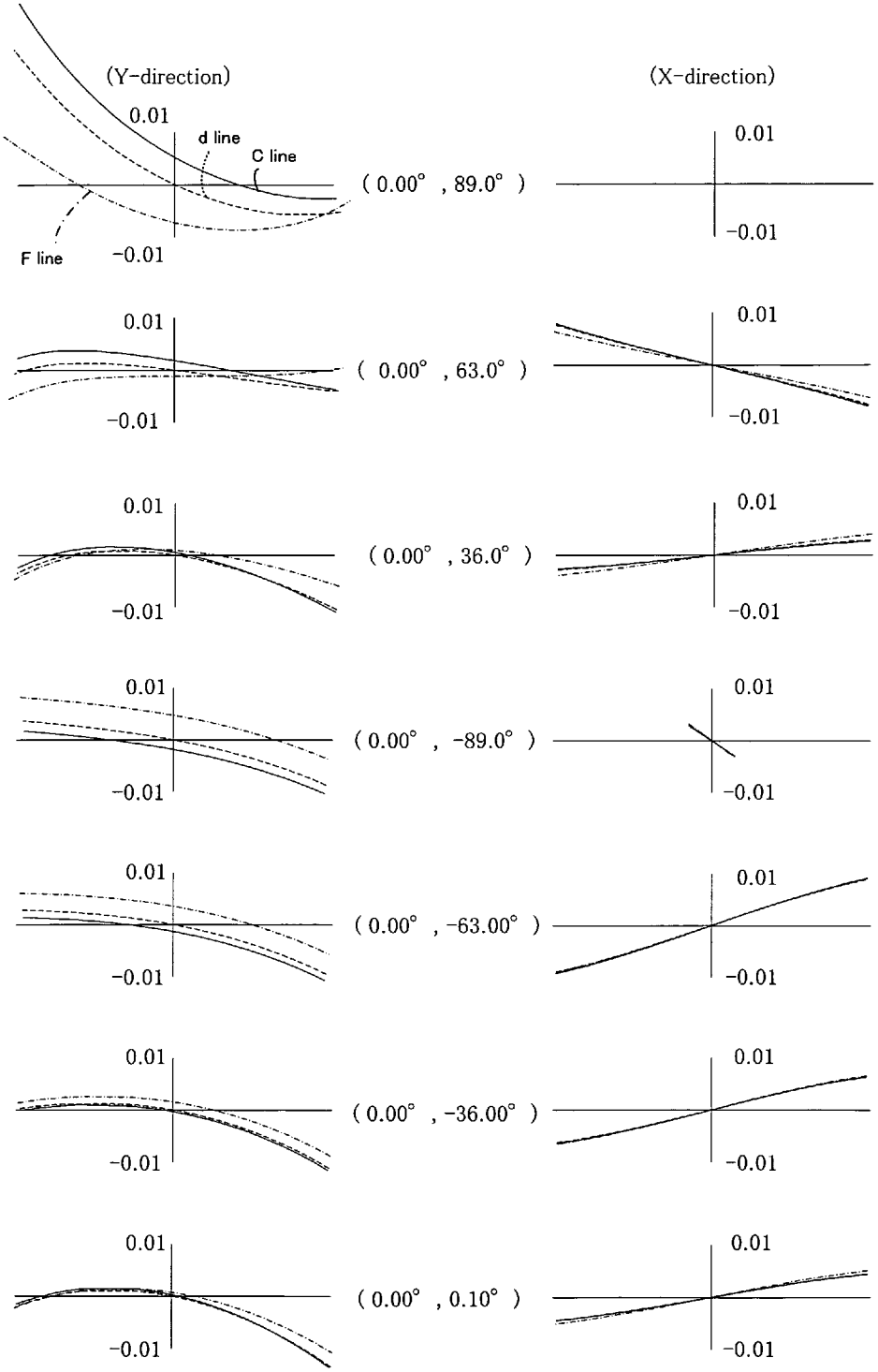
FIG. 11 is a schematic illustration of the transverse aberrations of the overall optical system of Example 3.
Figure 12:
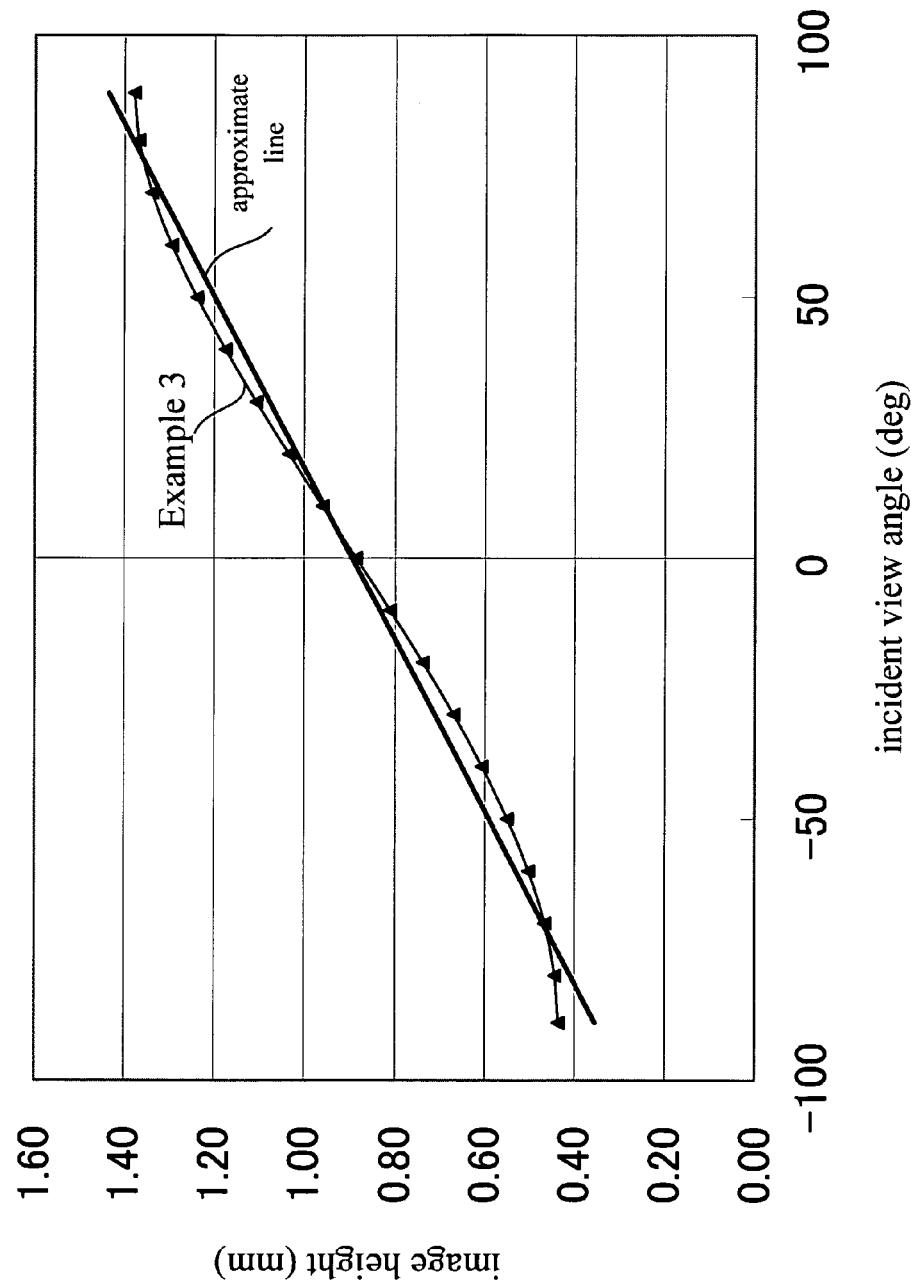
FIG. 12 is an F-θ graph of the overall optical system of Example 3.

FIG. 10 is a schematic cross-sectional view of the optical system 1 of Example 3 of the present invention taken along the central axis 2 thereof. FIG. 11 is a schematic illustration of the transverse aberrations of the overall optical system of this example. FIG. 12 is a graph indicating the relationship between the view angle and the image height. In the view representing the transverse aberrations, each pair of angle values represented at the center indicates (the view angle in the horizontal direction, the view angle in the vertical direction). The transverse aberrations in the Y direction (the meridional direction) and those in the X-direction (the sagittal direction) are also denoted. Note that a negative view angle in the horizontal direction denotes a clockwise angle observed by facing in the positive direction of the Y-axis, whereas a negative view angle in the vertical direction also denotes a clockwise angle observed by facing in the positive direction of the X-axis. This note is also applicable in the following similar descriptions.

In this example, none of the transmissive surfaces and the reflective surfaces of the transparent medium, that is concentric with and rotationally symmetric relative to the central axis 2 of the optical system 1 and has a refractive index greater than 1, is shared in the optical path and hence all the surfaces are different surfaces.

The optical system 1 includes a front group Gf that is rotationally symmetric relative to the central axis 2, a back group Gb that is also rotationally symmetric relative to the central axis 2 and an aperture S arranged between the front group Gf and the back group Gb so as to be coaxial with the central axis 2. The front group Gf includes a first group G1 and a second group G2, while the back group Gb includes a third group G3 and a fourth group G4.

The first group is formed by a transparent medium L1 that is rotationally symmetric relative to the central axis 2 and has a refractive index greater than 1. The transparent medium L1 has a cylindrical first transmissive surface 11 that is arranged at the external side vis-a-vis the object surface so as to be parallel to the central axis 2, a first reflective surface 12 that is formed by an extended rotary free curved surface in the inside of the transparent medium L1 at the side of the central axis 2 relative to the first transmissive surface 11 and has negative power, a second reflective surface 13 that is formed by an extended rotary free curved surface in the inside of the transparent medium L1 at the side opposite to the image plane 5 relative to the first reflective surface 12 and has positive power and a second transmissive surface 14 that is formed by an aspheric surface at the side of the image plane 5 relative to the second reflective surface 13 and has negative power.

The second group is formed by a positive meniscus lens L2 with its convex surface directed to the image plane 5 and has a third transmissive surface 21 and a fourth transmissive surface 31 arranged at the side of the image plane 5 relative to the third transmissive surface 21.

The third group G3 is formed by a cemented lens of a negative meniscus lens L3 with its concave surface directed to the image plane 5 and a double convex positive lens L4 and has a fifth transmissive surface 31, a cementing surface 34 arranged at the side of the image plane 5 relative to the fifth transmissive surface 31 and a sixth transmissive surface 41 arranged at the side of the image plane 5 relative to the cementing surface 34.

The fourth group is formed by a cemented lens of a double convex positive lens L5 and a double concave negative lens L6 and has a seventh transmissive surface 51, a cementing surface 56 arranged at the side of the image plane 5 relative to the seventh transmissive surface 51 and an eighth transmissive surface 61 arranged at the side of the image plane 5 relative to the cementing surface 56.

The optical system 1 forms an optical path A. As for the optical path A, the flux of light entering it from the object surface 3 of the optical system 1 proceeds sequentially by way of the front group Gf and the back group Gb and forms an annular image off the central axis 2 of the image plane 5 extending perpendicularly relative to the central axis 2.

The flux of light entering the optical system 1 to proceed along the optical path A goes into the transparent medium L1 of the first group of the front group Gf by way of the first transmissive surface 11 so as to be reflected by the first reflective surface 12 to the side opposite to the image plane 5 and then by the second reflective surface 13 to the side of the image plane 5 to form a subsequently Z-shaped optical path before going out from the transparent medium L1 by way of the second transmissive surface 14. Thereafter, it enters the positive meniscus lens L2 of the second group by way of the third transmissive surface 21 and goes out from the fourth transmissive surface 31.

Subsequently, the flux of light goes into the cemented lens of the negative meniscus lens L3 and the double convex positive lens L4 of the third group of the back group Gb at the opposite side relative to the central axis 2 by way of the aperture S that is arranged between the front group Gf and the back group Gb coaxially with the central axis 2 to operate as a stop and the fifth transmissive surface 31 and goes out from the sixth transmissive surface 41 by way of the cementing surface 34. Then, it goes into the cemented lens of the double convex positive lens L5 and the double concave negative lens L6 of the fourth group by way of the seventh transmissive surface 51 and goes out from the eighth transmissive surface 61 by way of the cementing surface 56 to form an image at a radially predetermined position off the central axis 2 of the image plane 5.

The specifications of Example 3 are as follows.

| view angle | −89° to 89° |
|---|---|
| image size | ⌀0.44 to ⌀2.38 |
| F number | 5.9 |

Examples 1 through 3 represent the following values for $\beta\omega$, P2, Pm, D and Dr, where $\beta\omega$ is the angular magnification at the meridional cross section of the optical element, P2 is the power at the meridional cross section of the surface having the second transmission effect, Pm is the power of the entire optical system at the meridional cross section of the central principal ray of light, D is the external dimension of the optical element and Dr is the external dimension of the image.

|  | Example 1 | Example 2 | Example 3 |
|---|---|---|---|
| $\beta\omega$ | 0.099 | 0.090 | 0.129 |
| P2/Pm | −3.022 | −2.427 | −3.932 |
| D | 7.000 | 7.000 | 8.000 |
| Dr | 2.366 | 2.756 | 2.381 |
| D/Dr | 2.959 | 2.528 | 3.360 |

Some of the parameters of the above-described Examples 1 through 3 are listed below. In the table represented below, "ASS" denotes an aspheric surface and "ERFS" denotes an extended rotary free curved surface, while "RE" denotes a reflective surface.

EXAMPLE 1

| Surface number | Radius of curvature | Plane gap | Eccentricity | Refractive index | Abbe number |
|---|---|---|---|---|---|
| Object | ∞ | ∞ | eccentricity (1) | | |
| 1 | ERFS [1] | | eccentricity (2) | 1.8348 | 42.7 |
| 2 | ERFS [2] (RE) | | eccentricity (3) | 1.8348 | 42.7 |
| 3 | ERFS [3] (RE) | | eccentricity (4) | 1.8348 | 42.7 |
| 4 | ASS [1] | | eccentricity (5) | | |
| 5 | ∞ | 0.50 | eccentricity (6) | 1.5163 | 64.1 |
| 6 | ∞ (Stop) | 0.35 | | | |
| 7 | 2.82 | 0.30 | | 1.8467 | 23.8 |
| 8 | 1.28 | 1.20 | | 1.7440 | 44.8 |
| 9 | −1.85 | 0.10 | | | |
| 10 | 1.84 | 1.40 | | 1.4971 | 69.3 |
| 11 | −1.14 | 0.30 | | 1.8467 | 23.8 |
| 12 | 20.09 | 0.50 | | | |
| 13 | ∞ | 0.40 | | 1.5163 | 64.1 |
| 14 | ∞ | 0.10 | | | |
| Image surface | ∞ | | | | |

| ERFS [1] | |
|---|---|
| RY | ∞ |
| θ | 90.00 |
| R | −3.50 |

| ERFS [2] | |
|---|---|
| RY | 4.52 |
| θ | 39.68 |
| R | −2.18 |

-continued

| ERFS [3] | |
|---|---|
| RY | 5.72 |
| θ | 10.80 |
| R | −1.62 |

| ASS [1] | |
|---|---|
| R | 0.70 |
| k | −1.9423E−01 | eccentricity [1]

| | | | | | | |
|---|---|---|---|---|---|---|
| X | 0.00 | Y | 0.00 | Z | 0.00 | |
| α | 90.00 | β | 0.00 | γ | 0.00 | | eccentricity [2]

| | | | | | | |
|---|---|---|---|---|---|---|
| X | 0.00 | Y | 0.00 | Z | 0.00 | |
| α | 0.00 | β | 0.00 | γ | 0.00 | | eccentricity [3]

| | | | | | | |
|---|---|---|---|---|---|---|
| X | 0.00 | Y | 0.00 | Z | 0.00 | |
| α | 0.00 | β | 0.00 | γ | 0.00 | | eccentricity [4]

| | | | | | | |
|---|---|---|---|---|---|---|
| X | 0.00 | Y | 0.00 | Z | −2.95 | |
| α | 0.00 | β | 0.00 | γ | 0.00 | | eccentricity [5]

| | | | | | | |
|---|---|---|---|---|---|---|
| X | 0.00 | Y | 0.00 | Z | −1.46 | |
| α | 0.00 | β | 0.00 | γ | 0.00 | | eccentricity [6]

| | | | | | | |
|---|---|---|---|---|---|---|
| X | 0.00 | Y | 0.00 | Z | −0.10 | |
| α | 0.00 | β | 0.00 | γ | 0.00 | |

EXAMPLE 2

Side view optical path

| Surface number | Radius of curvature | Plane gap | Eccentricity | Refractive index | Abbe number |
|---|---|---|---|---|---|
| Object | ∞ | ∞ | eccentricity (1) | | |
| 1 | ERFS [1] | | eccentricity (2) | 1.8348 | 42.7 |
| 2 | ERFS [2] (RE) | | eccentricity (3) | 1.8348 | 42.7 |
| 3 | ERFS [3] (RE) | | eccentricity (4) | 1.8348 | 42.7 |
| 4 | ASS [1] | | eccentricity (5) | | |
| 5 | ∞ | 0.50 | eccentricity (6) | 1.5163 | 64.1 |
| 6 | ∞ (Stop) | 0.35 | | | |
| 7 | 2.77 | 0.30 | | 1.8467 | 23.8 |
| 8 | 1.39 | 1.20 | | 1.7012 | 44.8 |
| 9 | −1.79 | 0.10 | | | |
| 10 | 2.01 | 1.40 | | 1.4875 | 70.4 |
| 11 | −1.25 | 0.30 | | 1.8467 | 23.8 |
| 12 | 10.29 | 0.50 | | | |
| 13 | ∞ | 0.40 | | 1.5163 | 64.1 |
| 14 | ∞ | 0.10 | | | |
| Image surface | ∞ | | | | |

| ERFS [1] | |
|---|---|
| RY | ∞ |
| θ | 90.00 |
| R | −3.50 |

| ERFS [2] | |
|---|---|
| RY | 3.88 |
| θ | 39.86 |
| R | −2.34 |

| ERFS [3] | |
|---|---|
| RY | 5.61 |
| θ | 13.60 |
| R | −1.86 |

| ASS [1] | |
|---|---|
| R | 0.87 |
| k | −1.8327E−01 | eccentricity [1]

| | | | | | | |
|---|---|---|---|---|---|---|
| X | 0.00 | Y | 0.00 | Z | 0.00 | |
| α | 90.00 | β | 0.00 | γ | 0.00 | | eccentricity [2]

| | | | | | | |
|---|---|---|---|---|---|---|
| X | 0.00 | Y | 0.00 | Z | 0.00 | |
| α | 0.00 | β | 0.00 | γ | 0.00 | | eccentricity [3]

| | | | | | | |
|---|---|---|---|---|---|---|
| X | 0.00 | Y | 0.00 | Z | 0.00 | |
| α | 0.00 | β | 0.00 | γ | 0.00 | | eccentricity [4]

| | | | | | | |
|---|---|---|---|---|---|---|
| X | 0.00 | Y | 0.00 | Z | −2.64 | |
| α | 0.00 | β | 0.00 | γ | 0.00 | | eccentricity [5]

| | | | | | | |
|---|---|---|---|---|---|---|
| X | 0.00 | Y | 0.00 | Z | −1.55 | |
| α | 0.00 | β | 0.00 | γ | 0.00 | | eccentricity [6]

| | | | | | | |
|---|---|---|---|---|---|---|
| X | 0.00 | Y | 0.00 | Z | 0.13 | |
| α | 0.00 | β | 0.00 | γ | 0.00 | |

Direct view optical path

| Surface number | Radius of curvature | Plane gap | Eccentricity | Refractive index | Abbe number |
|---|---|---|---|---|---|
| Object | ∞ | ∞ | eccentricity (1) | | |
| 1 | 5.00 | | eccentricity (7) | 1.8348 | 42.7 |
| 2 | ASS [1] | | eccentricity (5) | | |
| 3 | ∞ | 0.50 | eccentricity (6) | 1.5163 | 64.1 |
| 4 | ∞ (Stop) | 0.35 | | | |
| 5 | 2.82 | 0.30 | | 1.8467 | 23.8 |
| 6 | 1.28 | 1.20 | | 1.7440 | 44.8 |
| 7 | −1.85 | 0.10 | | | |
| 8 | 1.84 | 1.40 | | 1.4971 | 69.3 |
| 9 | −1.14 | 0.30 | | 1.8467 | 23.8 |
| 10 | 20.09 | 0.50 | | | |
| 11 | ∞ | 0.40 | | 1.5163 | 64.1 |
| 12 | ∞ | 0.10 | | | |
| Image surface | ∞ | | | | |

| ASS [1] | |
|---|---|
| R | 0.70 |
| k | −1.9423E−01 | eccentricity [1]

| | | | | | | |
|---|---|---|---|---|---|---|
| X | 0.00 | Y | 0.00 | Z | 0.00 | |
| α | 90.00 | β | 0.00 | γ | 0.00 | | eccentricity [7]

| | | | | | | |
|---|---|---|---|---|---|---|
| X | 0.00 | Y | 0.00 | Z | −2.85 | |
| α | 0.00 | β | 0.00 | γ | 0.00 | | eccentricity [5]

| | | | | | | |
|---|---|---|---|---|---|---|
| X | 0.00 | Y | 0.00 | Z | −1.55 | |
| α | 0.00 | β | 0.00 | γ | 0.00 | | eccentricity [6]

| | | | | | | |
|---|---|---|---|---|---|---|
| X | 0.00 | Y | 0.00 | Z | 0.13 | |
| α | 0.00 | β | 0.00 | γ | 0.00 | |

EXAMPLE 3

| Surface number | Radius of curvature | Plane gap | Eccentricity | Refractive index | Abbe number |
|---|---|---|---|---|---|
| Object | ∞ | ∞ | eccentricity (1) | | |
| 1 | ERFS [1] | | eccentricity (2) | 1.8348 | 42.7 |
| 2 | ERFS [2] (RE) | | eccentricity (3) | 1.8348 | 42.7 |
| 3 | ERFS [3] (RE) | | eccentricity (4) | 1.8348 | 42.7 |
| 4 | ASS [1] | | eccentricity (5) | | |
| 5 | −1.45 | 0.50 | eccentricity (6) | 1.5163 | 64.1 |
| 6 | −1.21 | 0.10 | | | |
| 7 | ∞ (Stop) | 0.70 | | | |
| 8 | 2.51 | 0.30 | | 1.8467 | 23.8 |
| 9 | 1.50 | 0.80 | | 1.5831 | 62.4 |
| 10 | −2.32 | 1.47 | | | |
| 11 | 2.02 | 1.60 | | 1.6204 | 60.3 |
| 12 | −1.38 | 0.30 | | 1.8467 | 23.8 |
| 13 | ∞ | 0.31 | | | |
| 14 | ∞ | 0.40 | | 1.5163 | 64.1 |
| 15 | ∞ | 0.10 | | | |
| Image surface | ∞ | | | | |

ERFS [1]

| | |
|---|---|
| RY | ∞ |
| θ | 90.00 |
| R | −4.00 |

ERFS [2]

| | |
|---|---|
| RY | 4.80 |
| θ | 40.86 |
| R | −2.38 |
| C4 | −1.2352E−02 |

ERFS [3]

| | |
|---|---|
| RY | 6.57 |
| θ | 12.25 |
| R | −1.84 |
| C4 | −3.4641E−03 |

ASS [1]

| | |
|---|---|
| R | 0.58 |
| k | −1.3453E−01 | eccentricity [1]

| X | 0.00 | Y | 0.00 | Z | 0.00 |
|---|---|---|---|---|---|
| α | 90.00 | β | 0.00 | γ | 0.00 | eccentricity [2]

| X | 0.00 | Y | 0.00 | Z | 0.00 |
|---|---|---|---|---|---|
| α | 0.00 | β | 0.00 | γ | 0.00 | eccentricity [3]

| X | 0.00 | Y | 0.00 | Z | 0.00 |
|---|---|---|---|---|---|
| α | 0.00 | β | 0.00 | γ | 0.00 | eccentricity [4]

| X | 0.00 | Y | 0.00 | Z | −3.73 |
|---|---|---|---|---|---|
| α | 0.00 | β | 0.00 | γ | 0.00 | eccentricity [5]

| X | 0.00 | Y | 0.00 | Z | −1.77 |
|---|---|---|---|---|---|
| α | 0.00 | β | 0.00 | γ | 0.00 | eccentricity [6]

| X | 0.00 | Y | 0.00 | Z | −0.71 |
|---|---|---|---|---|---|
| α | 0.00 | β | 0.00 | γ | 0.00 |

While each of the transmissive surfaces and the reflective surfaces of the transparent medium that is concentric with and rotationally symmetric relative to the central axis 2 of the optical system 1 and has a refractive index greater than 1 is designed as an extended rotary free curved surface in each of the above describe examples, an extended rotary free curved surface is equivalent to a spherical surface when the extended rotary free curved surface is orthogonal to a rotationally symmetric surface and does not involve any term of higher degree.

While each of the reflective surfaces and the refractive surfaces of the front group Gf is designed as an extended rotary free curved surface that is formed by rotating a line segment of an arbitrary shape around the central axis 2 and does not have the surface vertex on the central axis 2, it may be replaced by an arbitrary curved surface.

Figure 13:
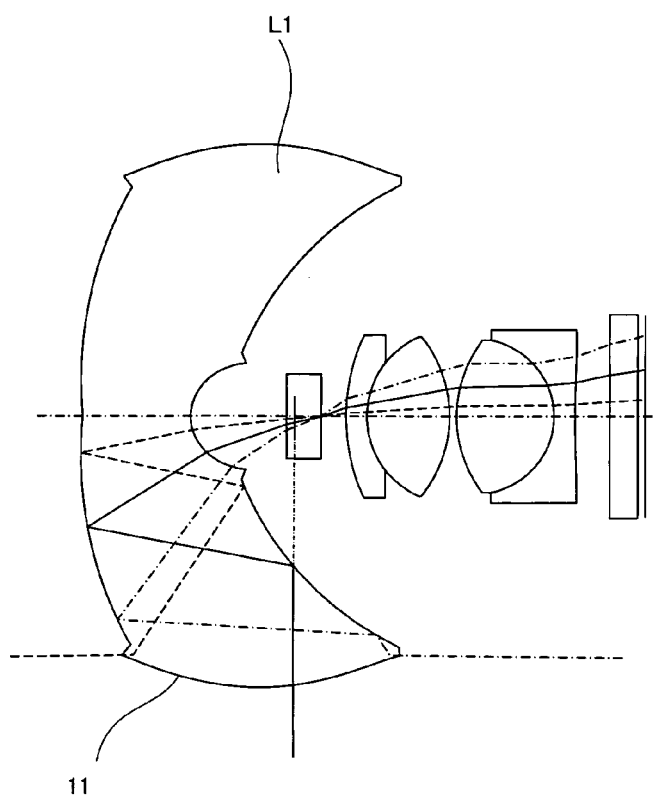
FIG. 13 is a schematic illustration of another example.
Figure 14:
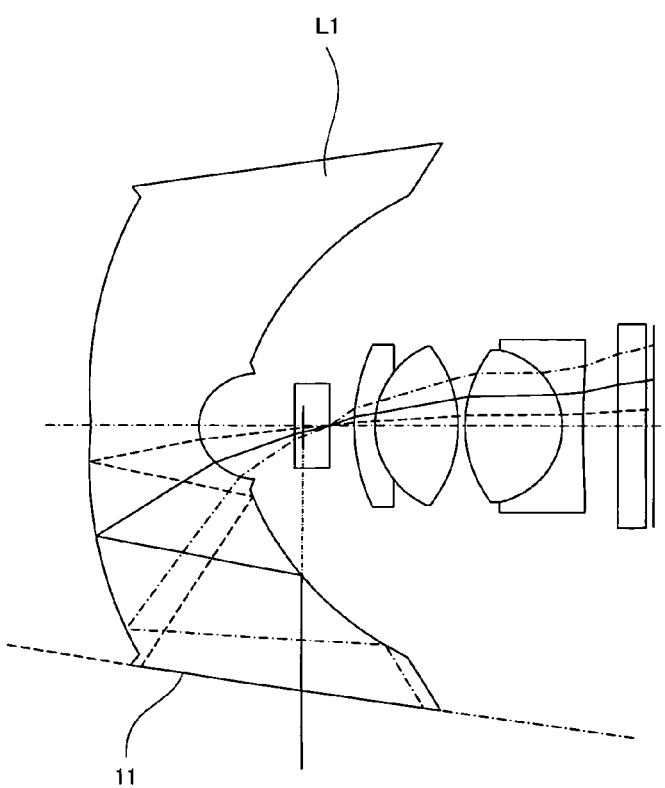
FIG. 14 is a schematic illustration of still another example.

For example, the first transmissive surface 11 needs to be formed in an outer peripheral part of the transparent medium L1, its shape is not limited to a cylindrical surface and may alternatively be a toric surface as illustrated in FIG. 13 or a conical surface as illustrated in FIG. 14.

Additionally, in an optical system according to the present invention, the inclination of the image plane 5 that arises due to eccentricity and the pupil aberration that arises when the stop is back-projected are corrected by using a formula that involve one or more than one odd-number-th degree terms for the formula for defining a line segment of an arbitrary shape for forming a rotationally symmetric surface.

An image with an omni-directional view angle of 360° can be picked up and projected by using a transparent medium that is rotationally symmetric around the central axis 2 of the front group Gf for the purpose of the present invention. However, an image with a view angle of 180°, 120°, 240° or some other angle may be picked up or projected by cutting the transparent medium along a cross section that includes the central axis 2 to a half, one-third, two-third or the like.

An optical system according to the present invention is described above as an image pickup or observation optical system that can obtain an image with an omni-directional (all-around) view angle of 360° including the vertex and the central axis (axis of rotational symmetry) 2 vertically directed, the present invention is not limited to image pickup optical systems and observation optical systems and an optical system according to the present invention can be used as a projection optical system for projecting an image with an omni-directional (all-around) view angle of 360° including the vertex where the optical path is followed reversely. Furthermore, an optical system according to the present invention can be used as an omni-directional optical system of an endoscope or an intra-canal observation apparatus.

Now, the optical elements and the optical systems including them according to the present invention will be described below by way of Example 4 and Example 5.

Figure 16:
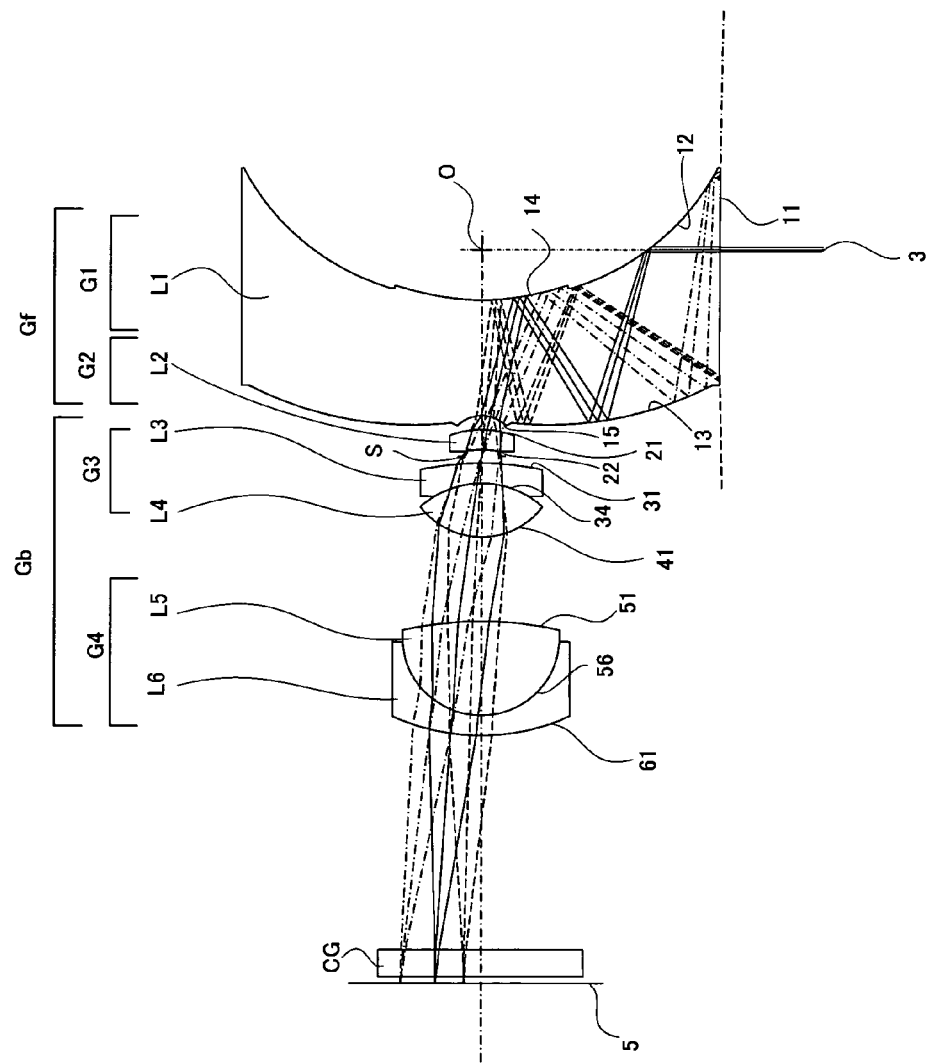
FIG. 16 is a schematic cross-sectional view of the optical system of Example 4 of the present invention taken along the central axis thereof.

FIG. 16 is a schematic cross-sectional view of the optical system 1 of Example 4 of the present invention, which will be described in greater detail hereinafter, taken along the central axis (axis of rotational symmetry) 2 thereof. Note that, while the optical system is described below in terms of image formation optical system, it is also applicable to a projection optical system by using the optical path reversely.

The optical system 1 of Example 4 includes a front group Gf that is rotationally symmetric relative to central axis 2 and has negative power, an aperture S and a back group Gb having positive power and can form or project an image without forming an intermediate image on any optical path. The parallel flat plate near the image plane 5 is typically a cover glass C for the imaging element.

The optical system becomes of a so-called retro-focus type when the front group Gf is made negative and the back group is made positive. Such an arrangement is effective particularly when a wide view angle needs to be secured for observation.

An optical element according to the present invention has a view angle of about 90° at a side in a cross section including the central axis 2 thereof and as viewed from a direction orthogonal relative to the central axis 2 and is made of a transparent medium L1 rotationally symmetric relative to the central axis 2 with a refractive index greater than 1, that the transparent medium L1 has a first transmissive surface 11 arranged at the outermost periphery relative to the central axis 2, a first reflective surface 12 arranged at the side of the central axis relative to the first transmissive surface, a second reflective surface 13 arranged at the side opposite to the image plane 5 relative to the first reflective surface 12, a third reflective surface 14 arranged at the side opposite to the image plane 5 relative to the second reflective surface 13 and a second transmissive surface 15 arranged at the side of the image plane 5 relative to the third reflective surface 14 and the flux of light entering the transparent medium L1 goes into the transparent medium L1 by way of the first transmissive surface 11 so as to be reflected to the side of the image plane 5 by the first reflective surface 12, then to the side opposite to the image plane 5 by the second reflective surface 13 and then to the side of the image plane 5 by the third reflective surface 14 to form a substantially W-shaped optical path A before going out from the transparent medium L1 at the side of the image plane 5 by way of the second transmissive surface 15 in the order of forward ray tracing, the optical path A being formed only at a side of the central axis 2.

With the above-described arrangement, the angle of incidence relative to the first reflective surface 12, the second reflective surface 13 and the third reflective surface 14 of the optical path A can be made relatively small while a large view angle of about 90° can be secured at a side, the occurrence of eccentric aberration occurred at the reflective surface can be minimized. Additionally, the optical path does not cross the central axis 2 in the optical element to make it possible to reduce the thickness of the optical element as the optical path A is arranged only at a side of the central axis.

Preferably, an optical element according to the present invention satisfies the condition of $$0.01 < \beta\omega < 0.5 \qquad (1),$$

where $\beta\omega$ is the angular magnification of meridional cross section of the optical element.

This conditional formula indicates the angular reduction magnification at a meridional cross section. The load on the optical element becomes too large when the angular magnification falls below the lower limit of the conditional formula (1) so that the optical element may become abnormally large and/or expensive glass having an abnormally high refractive index may be required. The view angle reducing effect of the optical element is lost when the angular magnification exceeds the upper limit of the conditional formula (1) so that the view angle of the flux of light entering the back group may become very wide to increase the load on the back group.

Still preferably, an optical element according to the present invention satisfies the condition of $$0.02 < \beta\omega < 0.2 \qquad (1-1).$$

Preferably, an optical element according to the present invention satisfies the condition of $$-10 < P2/Pm < -1 \qquad (2),$$

where P2 is the power of the second transmissive surface 15 and Pm is the power of the entire optical system at the meridional cross section of the central principal ray of light.

The conditional formula (2) above indicates the ratio that the second transmissive surface 15 takes in the total power. The negative power of the second transmissive surface 15 becomes large to make it possible to reduce the angular magnification when the above ratio falls below the lower limit of the conditional formula (2), although the comatic aberration and the astigmatism that arise on this surface becomes too large for the other surfaces to correct them. The negative power of the second transmissive surface 15 becomes too small to make the angular magnification of the meridional cross section large as in the case of the conditional formula (1) when the above ratio exceeds the upper limit of the conditional formula (2). Then, the load of the back group becomes large to make the optical system inevitably bulky.

It is possible to reduce the aberrations when a medium having a refractive index not smaller than 1.5 is employed for the optical element and the surfaces having a reflective effect are formed by using internal reflective surfaces if compared with an arrangement where the surfaces having a reflective effect are formed by reflective surfaces. With such an arrangement, it is possible to form a compact and high-resolution optical system and, at the same time, integrate two reflective surfaces to a great advantage from the viewpoint of assemblage and adjustment.

Preferably, a medium having a refractive index not smaller than 1.7 is used for the optical element. The curvature of an internal reflective surface can be reduced (and hence the radius of curvature thereof can be increased) by using a medium having a high refractive index so that, particularly when forming an eccentric optical system as in the case of the present invention, the occurrence of eccentric aberration can be minimized to improve the resolution.

It is more preferable to use medium having a refractive index not smaller than 1.8 for the optical element. Then, the critical angle becomes equal to 33° to make it possible to form the first reflective surface as a total reflective surface. Then, no reflection coating is required to a great advantage from the viewpoint of processing and prevention of loss of quantity of light.

No reflective membrane is required when at least one of the first reflective surface 12, the second reflective surface 13 and the third reflective surface 14 is made to have a total reflection effect. Then, an optical system can be manufactured with ease and the reflectance becomes equal to 100% to make it possible to brightly pick up an image.

Additionally, the distortions at and near the view angle can be corrected when at least one of the first reflective surface 12, the second reflective surface 13 and the third reflective surface 14 is formed by an extended rotary free curved surface formed by rotating a line segment of arbitrary shape having no plane of symmetry around the central axis 2.

Still additionally, an optical element according to the present invention can be made to have a shape that is vertically asymmetric relative to the center of the view angle to make it advantageous for correcting aberrations when at least one of the surfaces that the transparent medium L1 has is formed by an extended rotary free curved surface formed by rotating a line segment of arbitrary shape including one or more than one odd-number-th degree terms.

All of the three reflective surfaces having a reflection effect are so arranged that the concave surfaces thereof are directed to the aperture S. Then, as a result, the reflective surfaces represent a negative-positive-negative power arrangement so that it can take a wide view angle with ease and comatic aberration hardly arises there.

Preferably, the second transmissive surface is a surface having strong negative power with its concave surface directed to the aperture side. The view angle of the ray of light entering the back group can be reduced to by turn reduce the load of correcting the aberrations of the back group. It is possible to realize a compact optical system with a small number of constituent surfaces by reducing the view angle of the ray of light passing through the surface and going out from the optical element.

Additionally, the front group and the back group are made well balanced to produce a favorable effect for downsizing and simplifying the optical system by arranging the optical element close to the object relative to the aperture. It is hardly possible to achieve a large angular magnification and the load of the other lenses is raised when the optical element is arranged near the aperture because the central ray of light of a meridional cross section and a ray of light having a large view angle are found close to each other in the vicinity of the aperture. Additionally, it is not possible to provide a wide view angle for the front group located at the side of the object relative to the aperture when the optical element is arranged at the image side of the aperture.

Still preferably, the optical system satisfies the condition of $$D/Dr<10 \qquad (3),$$

where D is the external dimension of the optical element and Dr is the external dimension of the image.

The outer diameter of the optical system becomes large relative to the imaging element when the above ratio exceeds the upper limit of the conditional formula (3). The size of an imaging element is determined to a certain extent as a function of its price and its noise. For example, it will be impossible to form a compact optical system as a whole when a ⅓ or ¼-inch high-resolution imaging element that can be obtained at relatively low cost is employed and the upper limit of the conditional formula (3) is exceeded.

More preferably, the optical system satisfies the condition of $$D/Dr<5 \qquad (3\text{-}1).$$

Still preferably, the outer diameter D of the optical element satisfies the condition of $$D<20 \text{ mm} \qquad (4).$$

In particular, when the optical element is used for an image pickup system of an endoscope, the condition of the conditional formula (4) is preferably satisfied to reduce the load on the part of the subject of examination.

More preferably, the outer diameter of the optical element satisfies the condition of $$D<10 \text{ mm} \qquad (4\text{-}1).$$

Now, Examples 6 through 10 of optical system according to the present invention will be described below. The parameters of the optical systems of these examples will be described hereinafter.

Figure 15:
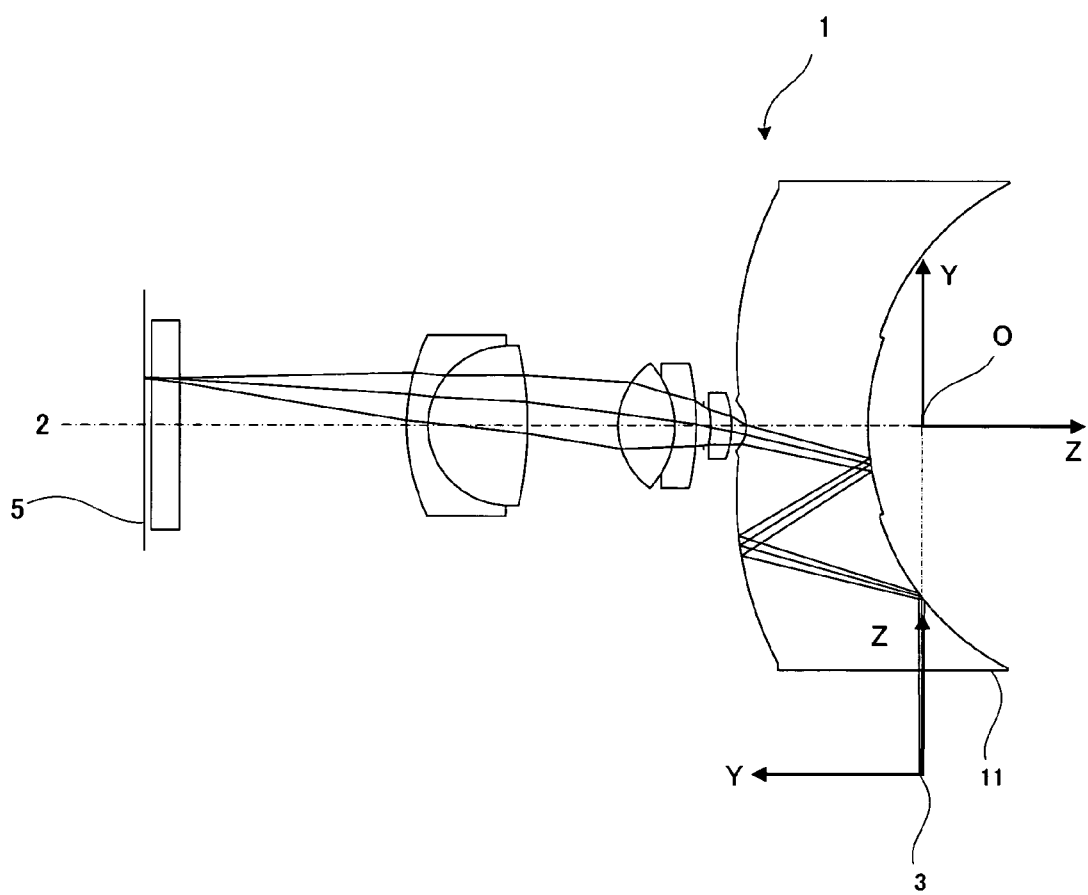
FIG. 15 is a schematic illustration of the coordinate system any of the optical system of Example 4 or Example 5 according to the present invention.

As coordinate system in forward ray tracing, for instance, the point of intersection of a prolonged line of the central principal ray of light proceeding from the object surface 3 toward the first surface and the central axis 2 is taken as origin O of eccentric optical surface and the direction orthogonal to the central axis 2 and of moving toward the side opposite to the object surface 3 as viewed from the central axis 2 is taken as a Y-axis positive direction as illustrated in FIG. 15, whereas the surface plane of the sheet of FIG. 15 is taken as a Y-Z plane. Then, the opposite direction of moving toward the image plane 5 in FIG. 15 is taken as a Z-axis positive direction and the axis that constitutes a right hand orthogonal coordinate system with the Y-axis and the Z-axis is taken as an X-axis positive direction.

As for the eccentric surface, the eccentricity from the origin O of the above optical system 1 that is used for defining the coordinate system that by turn defines the surface (as expressed by X, Y and Z respectively in the X-axis direction, the Y-axis direction and the Z-axis direction) and the angles of inclination of the planes extending respectively through the X-axis, the Y-axis and the Z-axis in the coordinate system that is defined by using the origin O of the optical system 1 ($\alpha$, $\beta$ and $\gamma$)(°) respectively) are given. Note that $\alpha$ and $\beta$ are taken as positive respectively in the counterclockwise directions relative to the positive direction of the X-axis and that of the Y-axis and $\gamma$ is taken as positive in the clockwise direction relative to the position direction of the Z-axis. Also note that each of the planes is rotated around the central axis thereof by $\alpha$, $\beta$ and $\gamma$ in such a way that the coordinate system that defines the planes is rotated firstly counterclockwise by $\alpha$ around the X-axis of the coordinate system that is defined by using the origin of the optical system and then the coordinate system obtained by rotating the initial coordinate system is rotated counterclockwise by $\beta$ around the Y-axis thereof. Then, finally, the coordinate system obtained by rotating the second coordinate system is rotated clockwise by $\gamma$ around the Z-axis thereof.

When a specific plane and the subsequent plane of the optical acting planes that the optical system of each of the examples includes form a coaxial optical system, the plane gap is given. Otherwise, the radius of curvature of each plane, the refractive index of the medium and the Abbe number are given according to the common practice.

All the terms relating to aspheric planes that are not described in the data on the constituent parameters that will be described hereinafter are equal to 0. The refractive index and the Abbe number relative to d-lines (wavelength: 587.56 nm) are given. The unit of length is mm. The eccentricity of each plane is expressed by the eccentricity from the reference plane as described above.

An aspheric plane is a rotationally symmetric defined by the formula represented below.

$$Z=(Y^2/R)/[1+\{1-(1+k)Y^2/R^2\}^{1/2}]+aY^4+bY^6+cY^8+dY^{10}+\ldots \qquad (a)$$

provided that Z is selected as an axis and Y denotes a direction perpendicular to the axis. In the above formula, R is the near-axis radius of curvature, k is the conic constant and a, b, c, d, . . . are respectively the aspheric surface coefficients of the fourth degree, the sixth degree, the eighth degree, the tenth degree and so on. The Z-axis of the above defining formula operates as the axis of a rotationally symmetric aspheric surface.

An extended rotary free curved surface is a rotationally symmetric surface given by the following definition.

Firstly, a curved line (b) that passes through the origin on the Y-Z coordinate plane as illustrated in FIG. 2 is defined.

$$Z=(Y^2/RY)/[1+\{1-(C_1+1)Y^2/RY^2\}^{1/2}]+C_2Y+C_3Y^2+C_4Y^3+C_5Y^4C_6Y^5+C_7Y^6+\ldots+C_{21}Y^{20}+\ldots+C_{n+1}Y^n+\ldots \qquad (b)$$

Then, curbed line F(Y) is defined by rotating the curbed line (b) by angle $\theta$(°), which is positive when it is rotated counterclockwise, facing in the positive direction of the X-axis. The curved line F(Y) also passes through the origin on the Y-Z coordinate plane.

The curved line F(Y) is translated in the direction of the positive direction of the Y-axis by distance R (in the negative direction of the Y-axis when it represents a negative value) and subsequently the translated curved line is rotated around the Z-axis to form a rotationally symmetric surface, which is an extended rotary free curved surface.

Then, as a result, the extended rotary free curved surface produces a free curved surface (free curved line) in the Y-Z plane and a circle of radius |R| in the X-Y plane.

From the above definition, the Z-axis operates as the axis (the axis of rotational symmetry) of the extended rotary free curved surface.

In the above formula (b), RY is the radius of curvature of the sphere term in the Y-Z cross section, $C_1$ is the conic constant and $C_2, C_3, C_4, C_5, \ldots$ are respectively the aspheric coefficients of the first degree, the second degree, the third degree, the fourth degree and so on.

Note that a surface of circular cone whose central axis is parallel to the Z-axis is given as an extended rotary free curved surface with $RY=\infty$, $C_1, C_2, C_3, C_4, C_5, \ldots =0$, $\theta$=(the angle of inclination of the surface of circular cone) and R=(the radius of the bottom in the X-Z plane).

All the terms relating to aspheric planes that are not described in the data on the constituent parameters that will be described hereinafter are equal to 0. The refractive index and the Abbe number relative to d-lines (wavelength: 587.56 nm) are given. The unit of length is mm. The eccentricity of each plane is expressed by the eccentricity from the reference plane as described above.

Figure 17:
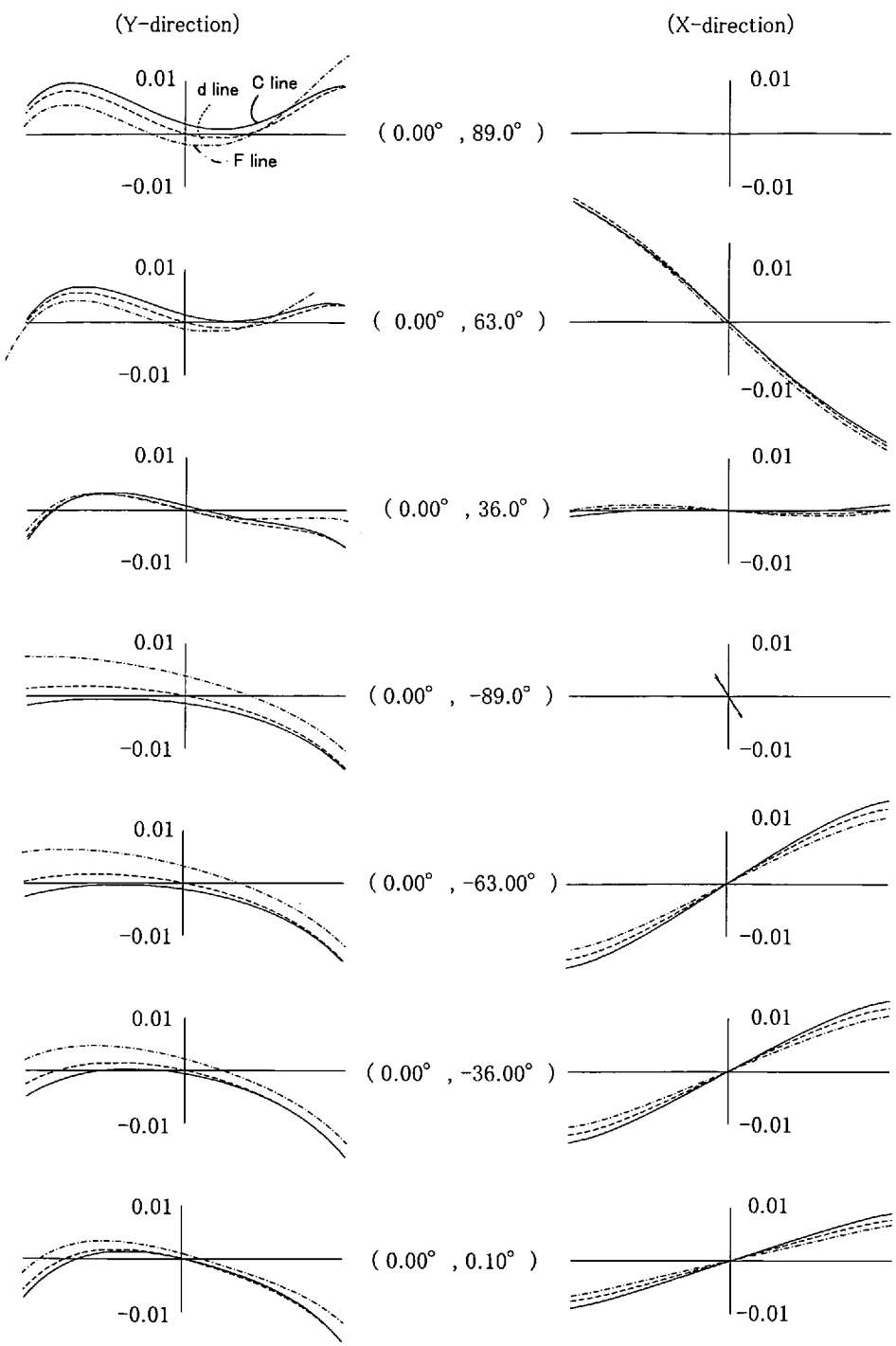
FIG. 17 is a schematic illustration of the transverse aberrations of the overall optical system of Example 4 of the present invention.
Figure 18:
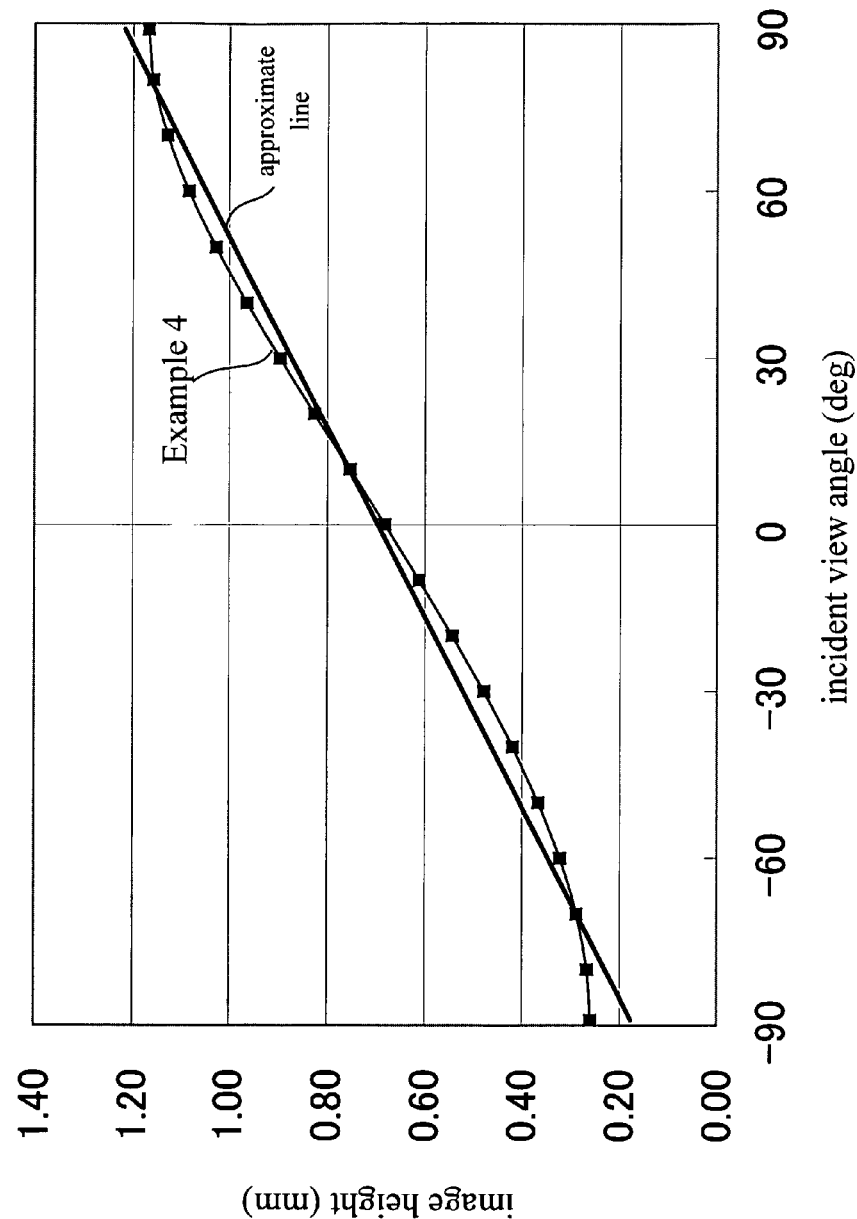
FIG. 18 is a schematic illustration of the image height relative to the view angle of the overall optical system of Example 4.

FIG. 16 is a schematic cross-sectional view of the optical system 1 of Example 4 of the present invention taken along the central axis 2 thereof. FIG. 17 is a schematic illustration of the transverse aberrations of the overall optical system of this example. FIG. 18 is a graph indicating the relationship between the view angle and the image height. In the view representing the transverse aberrations, each pair of angle values represented at the center indicates (the view angle in the horizontal direction, the view angle in the vertical direction). The transverse aberrations in the Y direction (the meridional direction) and those in the X-direction (the sagittal direction) are also denoted. Note that a negative view angle in the horizontal direction denotes a clockwise angle observed by facing in the positive direction of the Y-axis, whereas a negative view angle in the vertical direction also denotes a clockwise angle observed by facing in the positive direction of the X-axis. This note is also applicable in the following similar descriptions.

In this example, none of the transmissive surfaces and the reflective surfaces of the transparent medium, that is concentric with and rotationally symmetric relative to the central axis 2 of the optical system 1 and has a refractive index greater than 1, is shared in the optical path and hence all the surfaces are different surfaces.

The optical system 1 includes a front group Gf that is rotationally symmetric relative to the central axis 2, a back group Gb that is also rotationally symmetric relative to the central axis 2 and an aperture S arranged between the front group Gf and the back group Gb so as to be coaxial with the central axis 2. The front group includes a first group G1 and a second group G2, while the back group Gb includes a third group G3 and a fourth group G4.

The first group G1 is formed by a transparent medium L1 that is rotationally symmetric relative to the central axis 2 and has a refractive index greater than 1. The transparent medium L1 has a first transmissive surface 11 that is formed by a cylindrical surface at the external side vis-a-vis the object surface so as to be parallel to the central axis 2, a first reflective surface 12 that is formed by a toric surface in the inside of the transparent medium L1 at the side of the central axis 2 relative to the first transmissive surface 11 and has negative power, a second reflective surface 13 that is formed by a toric surface in the inside of the transparent medium L1 at the side of the image plane 5 relative to the first reflective surface 12 and has positive power, a third reflective surface 14 that is formed by an aspheric surface at the side opposite to the image plane 5 relative to the second reflective surface 13 and has negative power and a second transmissive surface 15 that is formed by a spherical surface at the side of the image plane 5 relative to the third reflective surface 14 and has negative power.

The second group G2 is formed by a negative meniscus lens L2 with its concave surface directed to the image plane 5 and has a third transmissive surface 21 and a fourth transmissive surface 22 arranged at the side of the image plane 5 relative to the third transmissive surface 21.

The third group G3 is formed by a cemented lens of a negative meniscus lens L3 with its concave surface directed to the image plane 5 and a double convex positive lens L4 and has a fifth transmissive surface 31, a cementing surface 34 arranged at the side of the image plane 5 relative to the fifth transmissive surface 31 and a sixth transmissive surface 41 arranged at the side of the image plane 5 relative to the cementing surface 34.

The fourth group G4 is formed by a cemented lens of a double convex positive lens L5 and a negative meniscus lens L6 with its convex surface directed to the image plane 5 and has a seventh transmissive surface 51, a cementing surface 56 arranged at the side of the image plane 5 relative to the seventh transmissive surface 51 and an eighth transmissive surface 61 arranged at the side of the image plane 5 relative to the cementing surface 56.

The optical system 1 forms an optical path A. As for the optical path A, the flux of light entering it from the object surface 3 proceeds sequentially by way of the front group Gf and the back group Gb and forms an annular image off the central axis 2 of the image plane 5 extending perpendicularly relative to the central axis 2.

The flux of light entering the optical system 1 to proceed along the optical path A goes into the transparent medium L1 of the first group G1 of the front group Gf by way of the first transmissive surface 11 so as to be reflected by the first reflective surface 12 to the side of the image plane 5, then by the second reflective surface 13 to the side opposite to the image plane 5 and then by the third reflective surface 14 to the side opposite to the image plane 5 to form a subsequently W-shaped optical path before going out from the transparent medium L1 by way of the second transmissive surface 15. Thereafter, it enters the negative meniscus lens L2 of the second group G2 by way of the third transmissive surface 21 and goes out from the negative meniscus lens L2 by way of the fourth transmissive surface 22 arranged at the side of the image plane 5 relative to the third transmissive surface 21.

Subsequently, the flux of light goes into the cemented lens of the negative meniscus lens L3 and the double convex positive lens L4 of the third group of the back group Gb at the opposite side relative to the central axis 2 by way of the aperture S that is arranged between the front group Gf and the back group Gb coaxially with the central axis 2 to operate as a stop and the fifth transmissive surface 31 and goes out from the sixth transmissive surface 41 by way of the cementing surface 34. Then, it goes into the cemented lens of the double convex positive lens L5 and the negative meniscus lens L6 of the fourth group by way of the seventh transmissive surface 51 and goes out from the eighth transmissive surface 61 by way of the cementing surface 56 to form an image at a radially predetermined position off the central axis 2 of the image plane 5.

The specifications of Example 4 are as follows.

| | |
|---|---|
| view angle | −89° to 89° |
| image size | ⌀0.51 to ⌀2.34 |
| F number | 8.5 |

Figure 19:
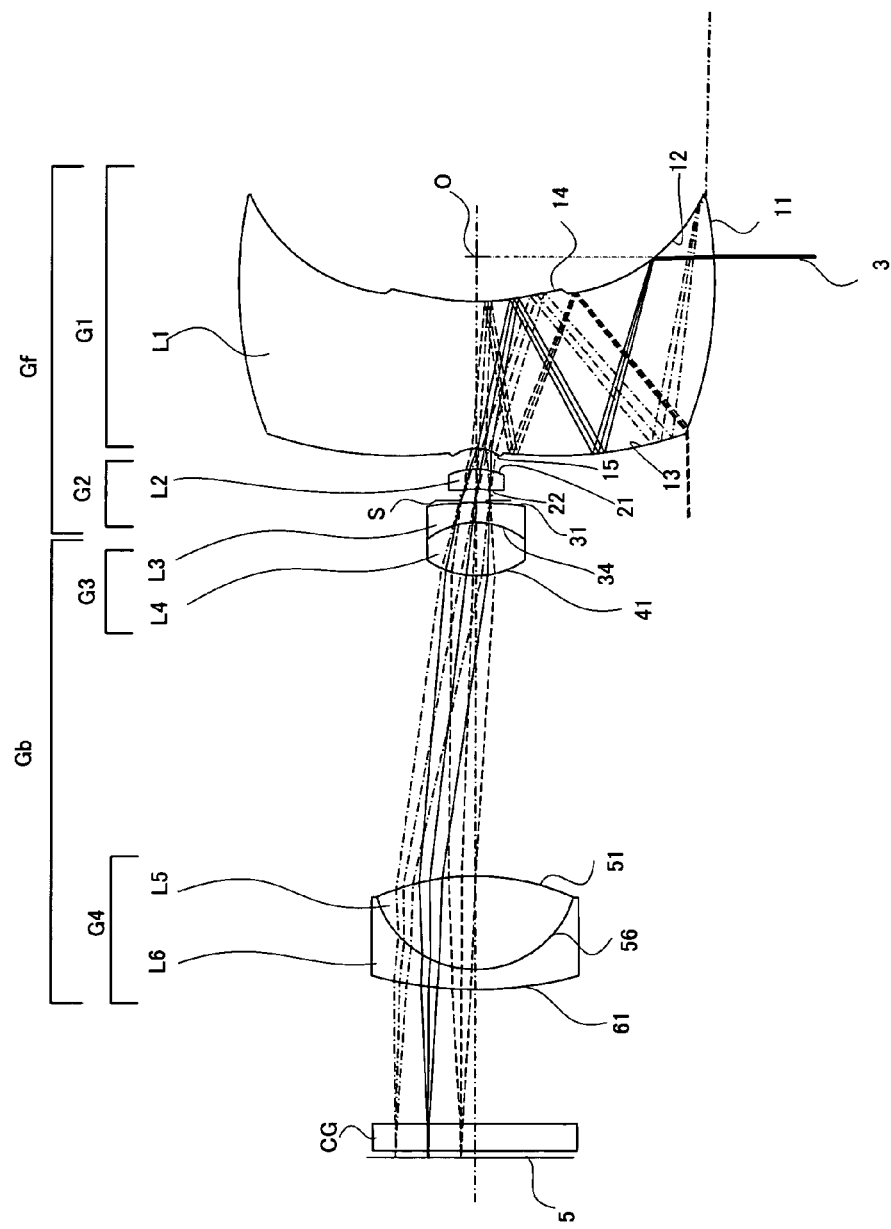
FIG. 19 is a schematic cross-sectional view of the optical system of Example 5 of the present invention taken along the central axis thereof.
Figure 20:
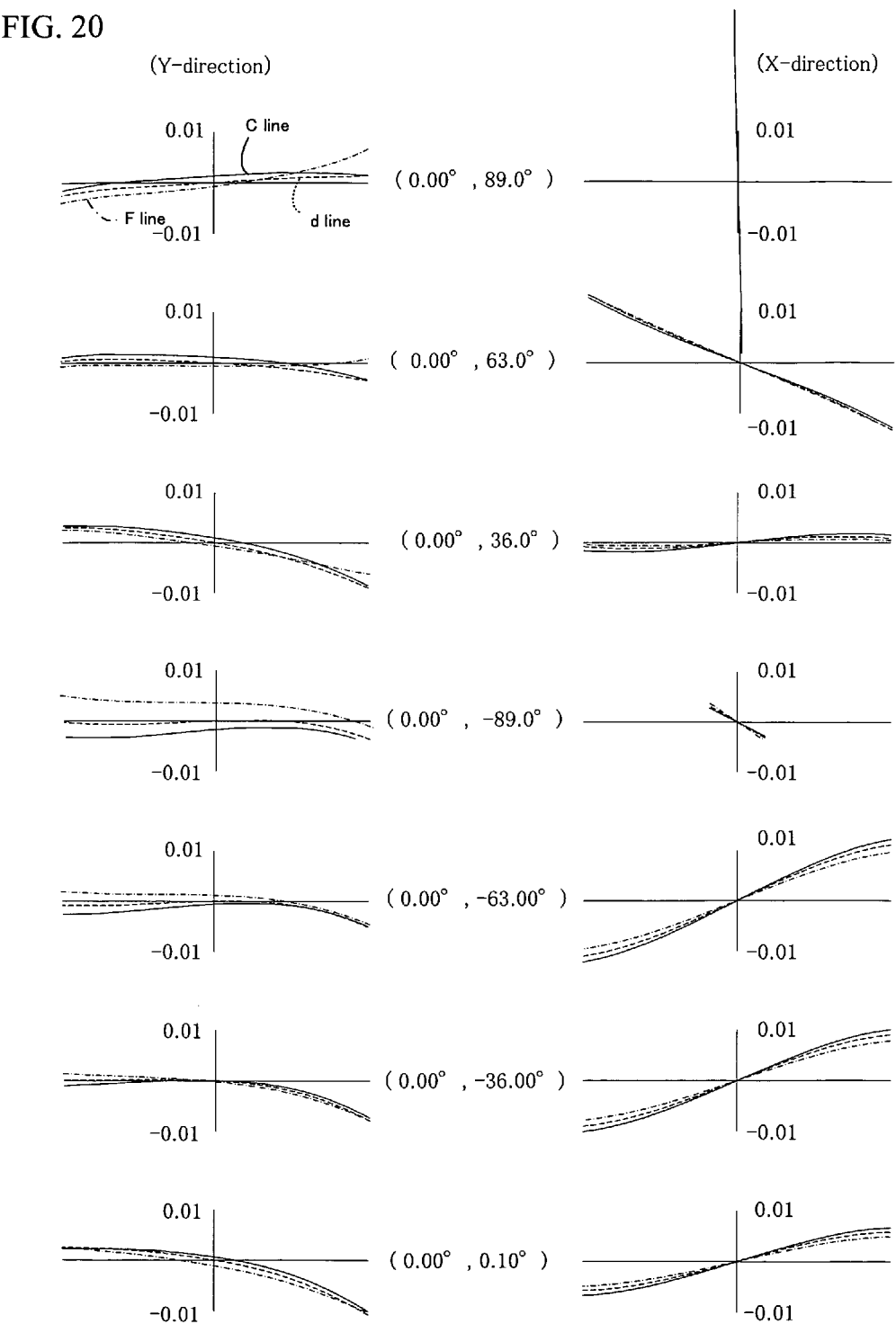
FIG. 20 is a schematic illustration of the transverse aberrations of the overall optical system of Example 5.
Figure 21:
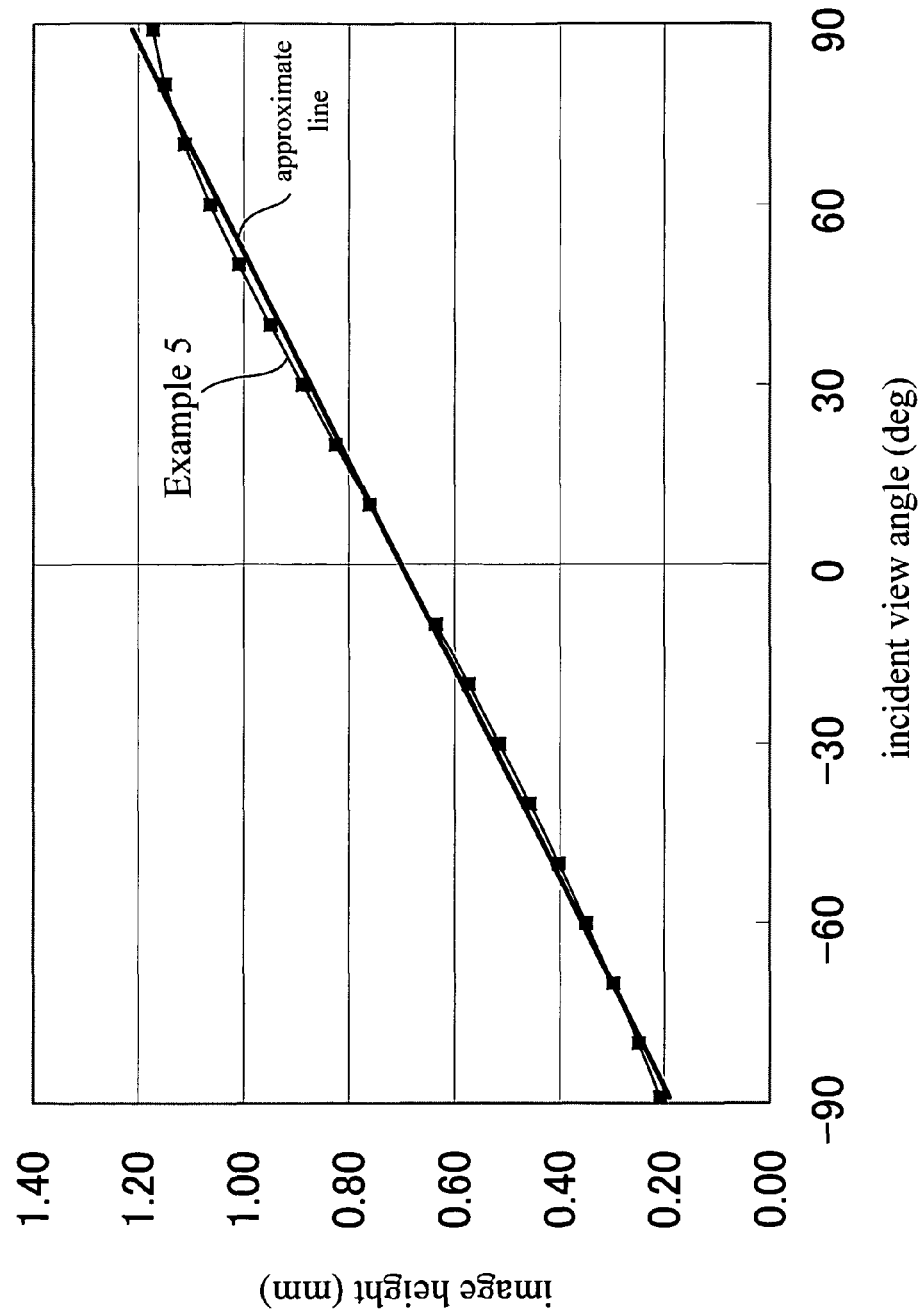
FIG. 21 is a schematic illustration of the image height relative to the view angle of the overall optical system of Example 5.

FIG. 19 is a schematic cross-sectional view of the optical system 1 of Example 5 taken along the central axis 2 thereof. FIG. 20 is a schematic illustration of the transverse aberrations of the overall optical system of this example. FIG. 21 is a graph indicating the relationship between the view angle and the image height.

In this example, none of the transmissive surfaces and the reflective surfaces of the transparent medium, that is concentric with and rotationally symmetric relative to the central axis 2 of the optical system 1 and has a refractive index greater than 1, is shared in the optical path and hence all the surfaces are different surfaces.

The optical system 1 includes a front group Gf that is rotationally symmetric relative to the central axis 2, a back group Gb that is also rotationally symmetric relative to the central axis 2 and an aperture S arranged between the front group Gf and the back group Gb so as to be coaxial with the central axis 2. The front group includes a first group G1 and a second group G2, while the back group Gb includes a third group G3 and a fourth group G4.

The first group G1 is formed by a transparent medium L1 that is rotationally symmetric relative to the central axis 2 and has a refractive index greater than 1. The transparent medium L1 has a first transmissive surface 11 that is formed by a toric surface at the external side vis-a-vis the object surface so as to be parallel to the central axis 2, a first reflective surface 12 that is formed by a toric surface in the inside of the transparent medium L1 at the side of the central axis 2 relative to the first transmissive surface 11 and has negative power, a second reflective surface 13 that is formed by a toric surface in the inside of the transparent medium L1 at the side of the image plane 5 relative to the first reflective surface 12 and has positive power, a third reflective surface 14 that is formed by an aspheric surface at the side opposite to the image plane 5 relative to the second reflective surface 13 and has negative power and a second transmissive surface 15 that is formed by a spherical surface at the side of the image plane 5 relative to the third reflective surface 14 and has negative power.

The second group G2 is formed by a negative meniscus lens L2 with its concave surface directed to the image plane 5 and has a third transmissive surface 21 and a fourth transmissive surface 22 arranged at the side of the image plane 5 relative to the third transmissive surface 21.

The third group G3 is formed by a cemented lens of a negative meniscus lens L3 with its concave surface directed to the image plane 5 and a double convex positive lens L4 and has a fifth transmissive surface 31, a cementing surface 34 arranged at the side of the image plane 5 relative to the fifth transmissive surface 31 and a sixth transmissive surface 41 arranged at the side of the image plane 5 relative to the cementing surface 34.

The fourth group G4 is formed by a cemented lens of a double convex positive lens L5 and a negative meniscus lens L6 with its convex surface directed to the image plane 5 and has a seventh transmissive surface 51, a cementing surface 56 arranged at the side of the image plane 5 relative to the seventh transmissive surface 51 and an eighth transmissive surface 61 arranged at the side of the image plane 5 relative to the cementing surface 56.

The optical system 1 forms an optical path A. As for the optical path A, the flux of light entering it from the object surface 3 of the optical system 1 proceeds sequentially by way of the front group Gf and the back group Gb and forms an annular image off the central axis 2 of the image plane 5 extending perpendicularly relative to the central axis 2.

The flux of light entering the optical system 1 to proceed along the optical path A goes into the transparent medium L1 of the first group G1 of the front group Gf by way of the first transmissive surface 11 so as to be reflected by the first reflective surface 12 to the side of the image plane 5, then by the second reflective surface 13 to the side opposite to the image plane 5 and then by the third reflective surface 14 to the side opposite to the image plane 5 to form a subsequently W-shaped optical path before going out from the transparent medium L1 by way of the second transmissive surface 15. Thereafter, it enters the negative meniscus lens L2 of the second group G2 by way of the third transmissive surface 21 and goes out from the negative meniscus lens L2 by way of the fourth transmissive surface 22 arranged at the side of the image plane 5 relative to the third transmissive surface 21.

Subsequently, the flux of light goes into the cemented lens of the negative meniscus lens L3 and the double convex positive lens L4 of the third group of the back group Gb at the opposite side relative to the central axis 2 by way of the aperture S that is arranged between the front group Gf and the back group Gb coaxially with the central axis 2 to operate as a stop and the fifth transmissive surface 31 and goes out from the sixth transmissive surface 41 by way of the cementing surface 34. Then, it goes into the cemented lens of the double convex positive lens L5 and the negative meniscus lens L6 of the fourth group by way of the seventh transmissive surface 51 and goes out from the eighth transmissive surface 61 by way of the cementing surface 56 to form an image at a radially predetermined position off the central axis 2 of the image plane 5.

The specifications of Example 5 are as follows.

| | |
|---|---|
| view angle | −89° to 89° |
| image size | ⌀0.41 to ⌀2.35 |
| F number | 10.42 |

Examples 4 and 5 represent the following values for βω, P2, Pm, D and Dr, where βω is the angular magnification at the meridional cross section of the optical element, P2 is the power at the meridional cross section of the surface having the second transmission effect, Pm is the power of the entire optical system at the meridional cross section of the central principal ray of light, D is the external dimension of the optical element and Dr is the external dimension of the image.

| | Example 4 | Example 5 |
|---|---|---|
| βω | 0.104 | 0.082 |
| P2/Pm | −4.173 | −3.969 |
| D | 7.000 | 7.000 |
| Dr | 2.337 | 2.345 |
| D/Dr | 2.996 | 2.985 |

Some of the parameters of the above-described Examples 4 and 5 are listed below. In the table represented below, "ASS" denotes an aspheric surface and "ERFS" denotes an extended rotary free curved surface, while "RE" denotes a reflective surface.

EXAMPLE 4

| Surface number | Radius of curvature | Plane gap | Eccentricity | Refractive index | Abbe number |
|---|---|---|---|---|---|
| Object | ∞ | | eccentricity (1) | | |
| 1 | ERFS [1] | | eccentricity (2) | 1.8348 | 42.7 |
| 2 | ERFS [2] (RE) | | eccentricity (3) | 1.8348 | 42.7 |
| 3 | ERFS [3] (RE) | | eccentricity (4) | 1.8348 | 42.7 |
| 4 | ASS [1] (RE) | | eccentricity (5) | 1.8348 | 42.7 |
| 5 | −0.50 | | eccentricity (6) | | |
| 6 | −1.31 | −0.30 | eccentricity (7) | 1.5163 | 64.1 |
| 7 | −1.28 | −0.10 | | | |
| 8 | ∞ (Stop) | −0.10 | | | |
| 9 | −4.27 | −0.30 | | 1.8467 | 23.8 |
| 10 | −1.33 | −0.80 | | 1.7440 | 44.8 |
| 11 | 1.11 | −1.26 | | | |
| 12 | −5.22 | −1.40 | | 1.5843 | 40.8 |
| 12 | 1.15 | −0.30 | | 1.8467 | 23.8 |
| 13 | 3.06 | −3.19 | | | |
| 14 | ∞ | −0.40 | | 1.5163 | 64.1 |
| 15 | ∞ | −0.10 | | | |
| Image surface | ∞ | | | | |

ERFS [1]

| | |
|---|---|
| RY | ∞ |
| θ | 90.00 |
| R | −3.50 |

ERFS [2]

| | |
|---|---|
| RY | 3.62 |
| θ | 37.06 |
| R | −2.44 |

ERFS [3]

| | |
|---|---|
| RY | 5.15 |
| θ | 8.06 |
| R | −1.71 |

ASS [1]

| | |
|---|---|
| R | 3.24 |
| k | −4.3870E+00 | eccentricity [1]

| X | 0.00 | Y | −10.00 | Z | 0.00 |
|---|---|---|---|---|---|
| α | 90.00 | β | 0.00 | γ | 0.00 | eccentricity [2]

| X | 0.00 | Y | −3.50 | Z | 0.00 |
|---|---|---|---|---|---|
| α | 0.00 | β | 0.00 | γ | 0.00 | eccentricity [3]

| X | 0.00 | Y | −2.44 | Z | 0.00 |
|---|---|---|---|---|---|
| α | 0.00 | β | 0.00 | γ | 0.00 | eccentricity [4]

| X | 0.00 | Y | 0.00 | Z | −2.55 |
|---|---|---|---|---|---|
| α | 0.00 | β | 0.00 | γ | 0.00 | eccentricity [5]

| X | 0.00 | Y | 0.00 | Z | −0.74 |
|---|---|---|---|---|---|
| α | 0.00 | β | 0.00 | γ | 0.00 | eccentricity [6]

| X | 0.00 | Y | 0.00 | Z | −2.47 |
|---|---|---|---|---|---|
| α | 0.00 | β | 0.00 | γ | 0.00 | eccentricity [7]

| X | 0.00 | Y | 0.00 | Z | −2.67 |
|---|---|---|---|---|---|
| α | 0.00 | β | 0.00 | γ | 0.00 |

EXAMPLE 5

| Surface number | Radius of curvature | Plane gap | Eccentricity | Refractive index | Abbe number |
|---|---|---|---|---|---|
| Object | ∞ | | eccentricity (1) | | |
| 1 | ERFS [1] | | eccentricity (2) | 1.8348 | 42.7 |
| 2 | ERFS [2] (RE) | | eccentricity (3) | 1.8348 | 42.7 |
| 3 | ERFS [3] (RE) | | eccentricity (4) | 1.8348 | 42.7 |
| 4 | ASS [1] (RE) | | eccentricity (5) | 1.8348 | 42.7 |
| 5 | −0.59 | | eccentricity (6) | | |
| 6 | −1.03 | −0.30 | eccentricity (7) | 1.5163 | 64.1 |
| 7 | −1.16 | −0.10 | | | |
| 8 | ∞ (Stop) | −0.10 | | | |
| 9 | −4.37 | −0.30 | | 1.8467 | 23.8 |
| 10 | −1.15 | −0.80 | | 1.7440 | 44.8 |
| 11 | 1.23 | −4.51 | | | |
| 12 | −3.47 | −1.40 | | 1.6148 | 36.9 |
| 12 | 1.51 | −0.30 | | 1.8467 | 23.8 |
| 13 | 5.76 | −2.01 | | | |
| 14 | ∞ | −0.40 | | 1.5163 | 64.1 |
| 15 | ∞ | −0.10 | | | |
| Image surface | ∞ | | | | |

ERFS [1]

| | |
|---|---|
| RY | 6.26 |
| θ | 93.53 |
| R | −3.50 |

ERFS [2]

| | |
|---|---|
| RY | 2.50 |
| θ | 38.21 |
| R | −2.60 |

ERFS [3]

| | |
|---|---|
| RY | 5.95 |
| θ | 6.60 |
| R | −1.81 |

ASS [1]

| | |
|---|---|
| R | 3.03 |
| k | −1.3118E+01 | eccentricity [1]

| X | 0.00 | Y | −10.00 | Z | 0.00 |
|---|---|---|---|---|---|
| α | 90.00 | β | 0.00 | γ | 0.00 | eccentricity [2]

| X | 0.00 | Y | 0.00 | Z | 0.00 |
|---|---|---|---|---|---|
| α | 0.00 | β | 0.00 | γ | 0.00 | eccentricity [3]

| X | 0.00 | Y | 0.00 | Z | −0.03 |
|---|---|---|---|---|---|
| α | 0.00 | β | 0.00 | γ | 0.00 | eccentricity [4]

| X | 0.00 | Y | 0.00 | Z | −2.94 |
|---|---|---|---|---|---|
| α | 0.00 | β | 0.00 | γ | 0.00 | eccentricity [5]

| X | 0.00 | Y | 0.00 | Z | −0.67 |
|---|---|---|---|---|---|
| α | 0.00 | β | 0.00 | γ | 0.00 | eccentricity [6]

| X | 0.00 | Y | 0.00 | Z | −2.87 |
|---|---|---|---|---|---|
| α | 0.00 | β | 0.00 | γ | 0.00 | eccentricity [7]

| X | 0.00 | Y | 0.00 | Z | −3.18 |
|---|---|---|---|---|---|
| α | 0.00 | β | 0.00 | γ | 0.00 |

Figure 22:
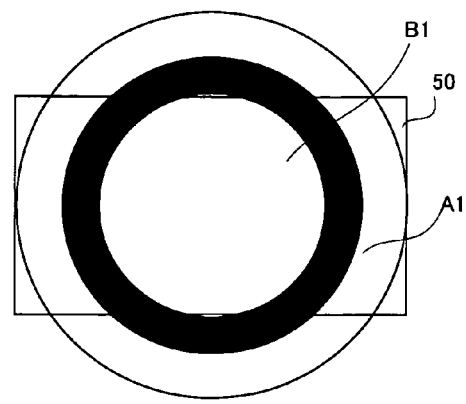
FIG. 22 is a schematic illustration of an exemplar positional arrangement of an image of the optical system and the imaging element of any of Examples 1 through 3 of the present invention.
Figure 22:
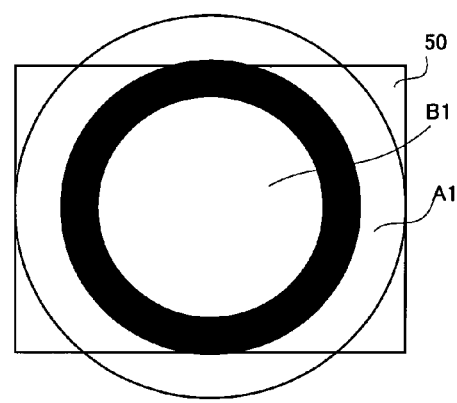
Figure 22:
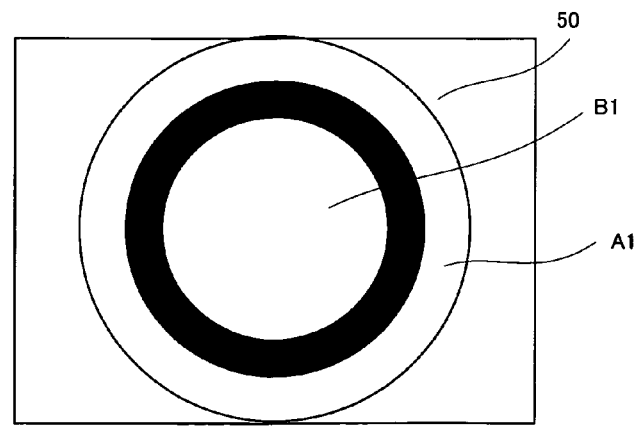

FIG. 22 is a schematic illustration of an exemplar positional arrangement of an image of an optical system according to Examples 1 through 3 and an imaging element. In FIG. 22, (a) is an example of using an imaging element with an aspect ratio of 16:9. When no vertically long image is used, the dimension of the imaging element 50 is preferably made equal to the distance between the left margin and the right margin of the image A1 of the side view optical path A. In FIG. 22, (b) is an example of using an imaging element 50 with an aspect ratio of 4:3 and making the dimension of the imaging element 50 agree with that of the image B1 of the direct view optical path B in a situation where no vertically long image is used as in (a) of FIG. 22. In FIG. 22, (c) is an example of using an imaging element 50 with an aspect ratio of 4:3 and making the dimension of the imaging element 50 agree with that of the image A1 of the side view optical path A. With this arrangement, both the image A1 of the side view optical path A and the image B1 of the direct view optical path B can be entirely picked up.

Figure 23:
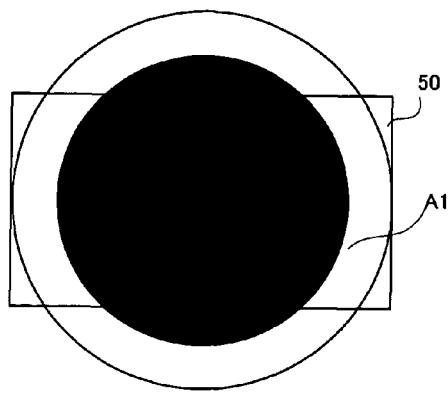
FIG. 23 is a schematic illustration of an exemplar positional arrangement of an image of the optical system and the imaging element of Example 4 or that of Example 5 of the present invention.
Figure 23:
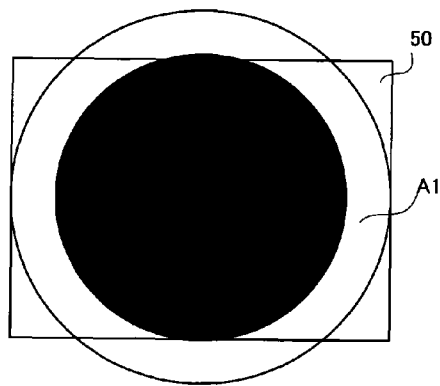
Figure 23:
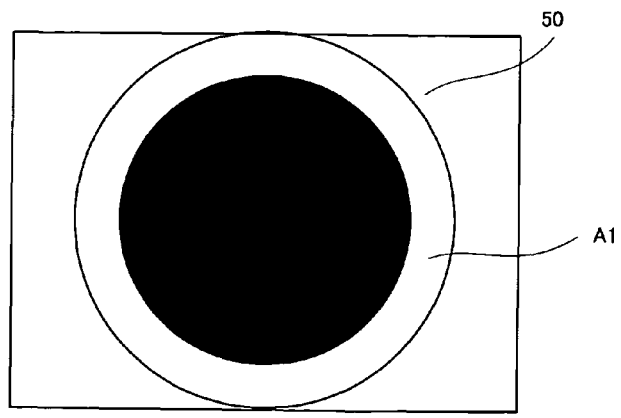

FIG. 23 is a schematic illustration of an exemplar positional arrangement of an image of an optical system according to Examples 4 and 5 and an imaging element. In FIG. 23, (a) is an example of using an imaging element with an aspect ratio of 16:9. When no vertically long image is used, the dimension of the imaging element 50 is preferably made equal to the distance between the left margin and the right margin of the image A1 of the optical path A. In FIG. 23, (b) is an example of using an imaging element 50 with an aspect ratio of 4:3 and making the dimension of the imaging element 50 where no vertically long image is used as in (a) of FIG. 23. In FIG. 23, (c) is an example of using an imaging element 50 with an aspect ratio of 4:3 and making the dimension of the imaging element 50 agree with that of the image A1 of the optical path A. With this arrangement, all the images A1 of the optical path A can be entirely picked up.

Figure 24:
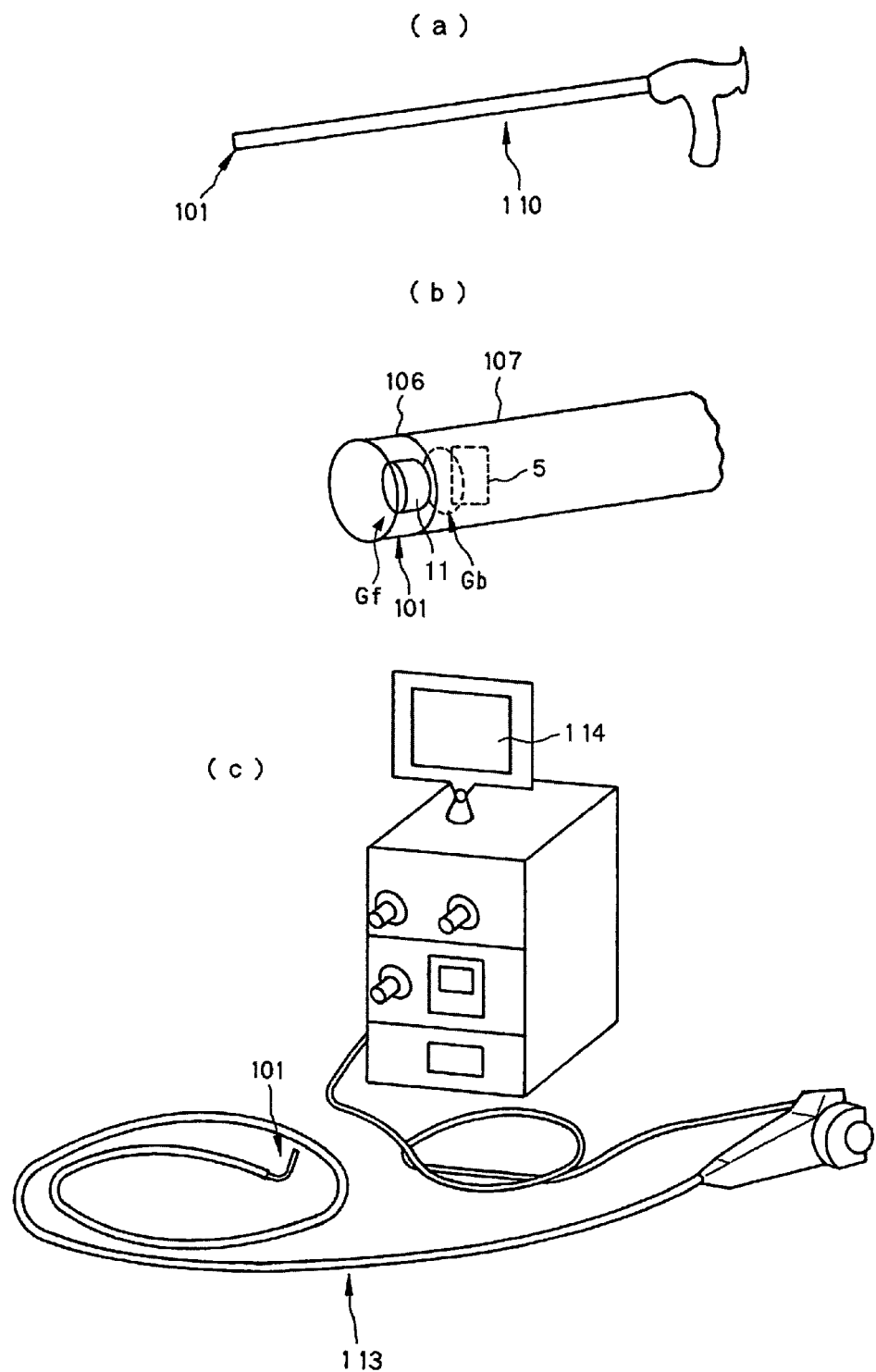
FIG. 24 is a schematic illustration of an example of using an optical system according to the present invention as an image pickup optical system at the front end of an endoscope.

Now, examples of using an image pickup optical system 101 and those of using a projection optical system 102 will be described below as applications of an optical system 1 according to the present invention. FIG. 24 is a schematic illustration of an example of using an image pickup optical system 101 according to the present invention as an image pickup optical system at the front end of an endoscope. In FIG. 24, (a) illustrates an example of mounting an image pickup optical system according to the invention to the front end 101 of a rigid endoscope 110 and picking up and observing a 360° omni-directional image. In FIG. 24, (b) schematically illustrates the configuration of the front end thereof. A flare stop 107 that is formed by a casing having a peripherally extending slit-like aperture 106 is arranged at the incident surface 11 of the front group Gf of a panoramic image pickup optical system 101 according to the present invention in order to prevent flare from entering. In FIG. 24, (c) illustrates an example of similarly mounting a panoramic image pickup optical system 101 according to the invention to the front end of a soft electronic endoscope 113 and displaying a picked up image on a display apparatus 114 after subjecting it to image processing.

Figure 25:
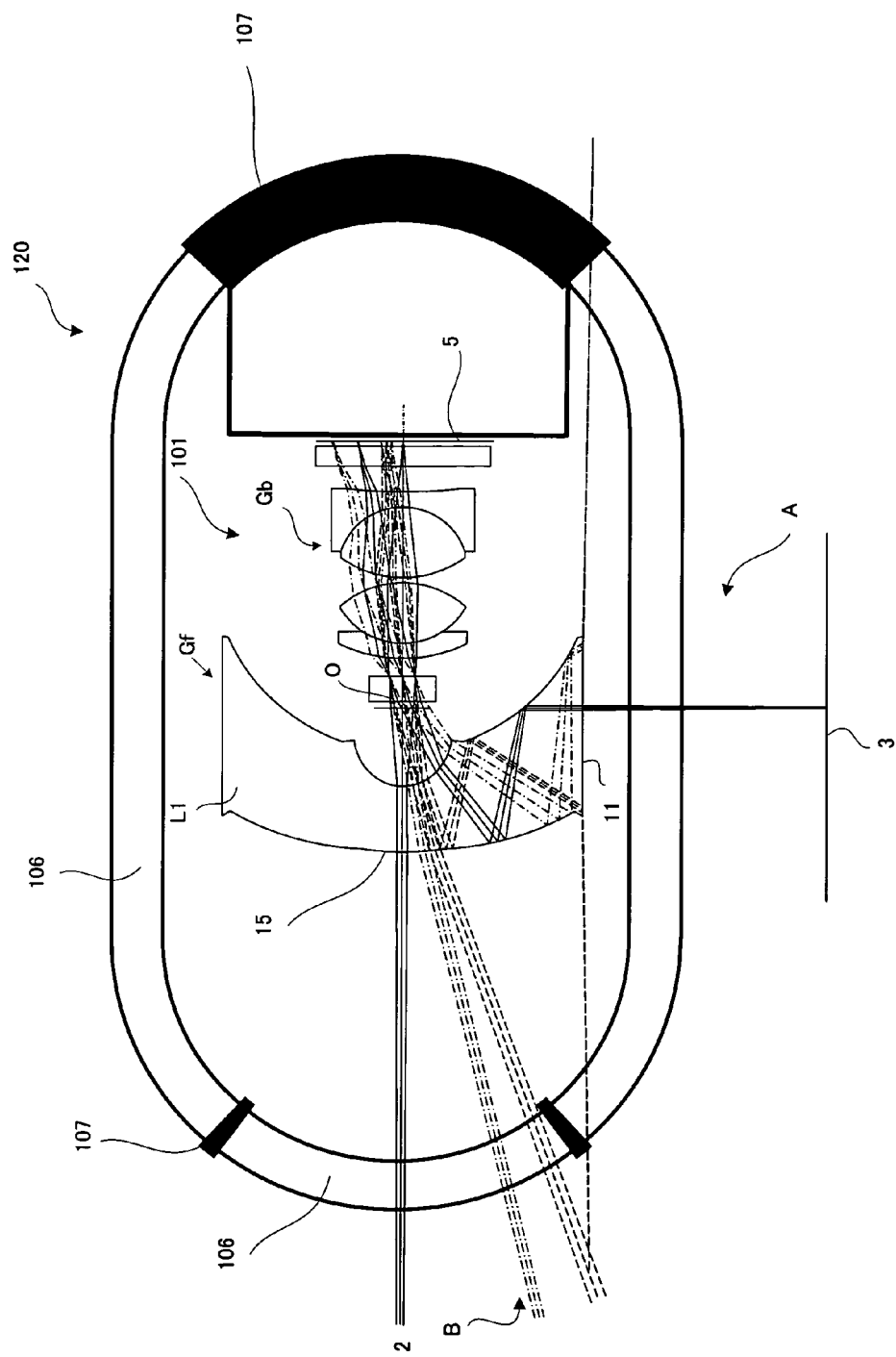
FIG. 25 is a schematic illustration of an example of using the optical system of Examples 1 through 3 of the present invention as an image pickup optical system of a capsule endoscope.

FIG. 25 is schematic illustrations of Example 1 of mounting an image pickup optical system 101 to a capsule endoscope 120 and picking up and observing a 360° omni-directional image. A flare stop 107 is formed at a casing having a peripherally extending slit-like aperture 106 around the side view first transmissive surface 11 of the front group Gf at the side view optical path A of an image pickup optical system 101 as well as a flare stop 107 is formed at a casing having a peripherally extending circular aperture 106 in front of the direct view first transmissive surface 15 of the front group Gf at the direct view optical path B of an image pickup optical system 101 according to the present invention in order to prevent flare from entering.

Figure 26:
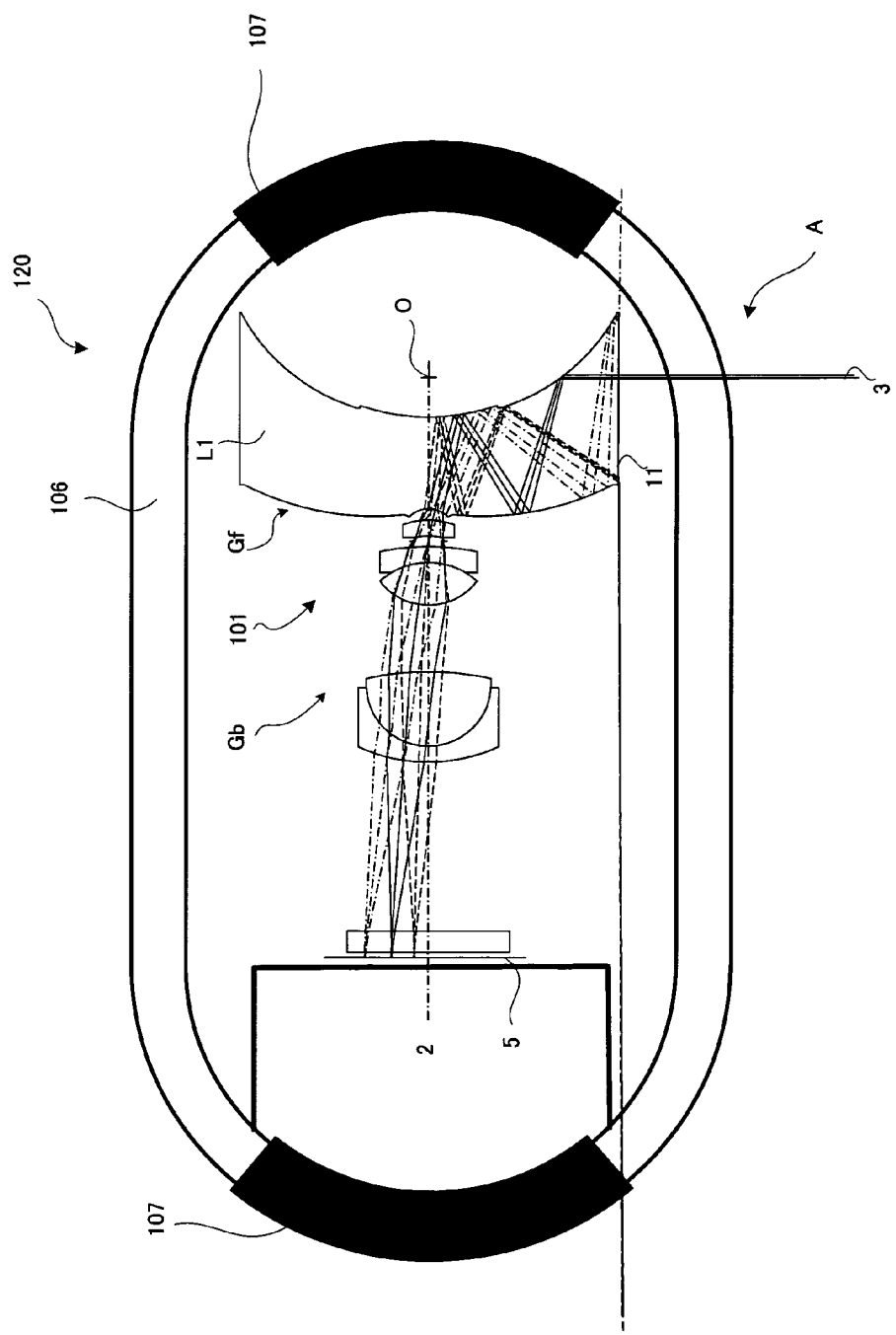
FIG. 26 is a schematic illustration of an example of using the optical system of Example 4 or Example 5 of the present invention as an image pickup optical system of a capsule endoscope.

FIG. 26 is schematic illustrations of Example 4 of mounting an image pickup optical system 101 to a capsule endoscope 120 and picking up and observing a 360° omni-directional image. A flare stop 107 is formed at a casing having a peripherally extending aperture 106 around of an image pickup optical system 101 according to the present invention in order to prevent flare from entering.

As illustrated in FIGS. 24, 25 and 26, an image of any of various parts can be picked up for observation from behind an image pickup optical system 101 according to the present invention when it is applied to an endoscope so that the part can be shot from various angles in order to pick up images therefore for the purpose of observation, although no such images can be picked up according to the conventional art.

Figure 27:
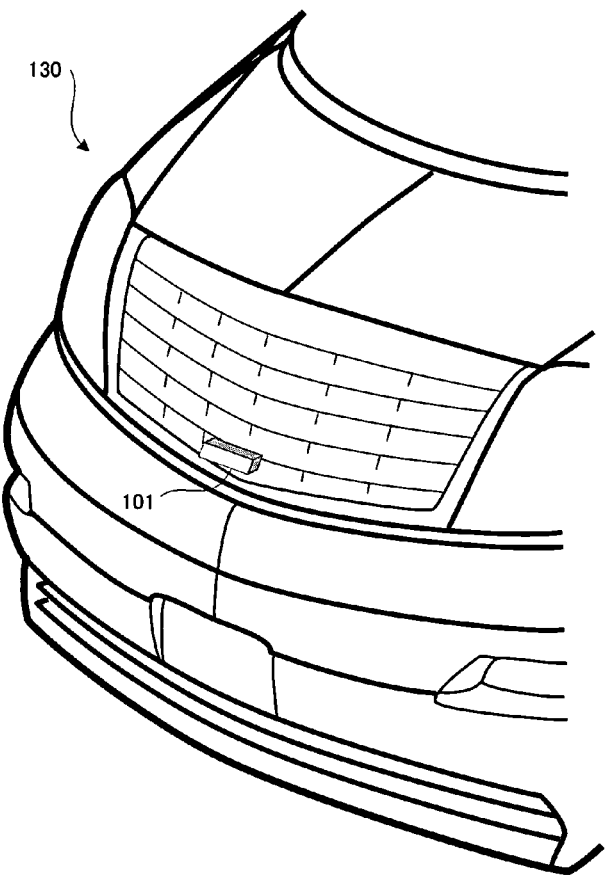
FIG. 27 is a schematic illustration of examples of using an optical system according to the present invention as an image pickup optical system of an automobile.
Figure 27:
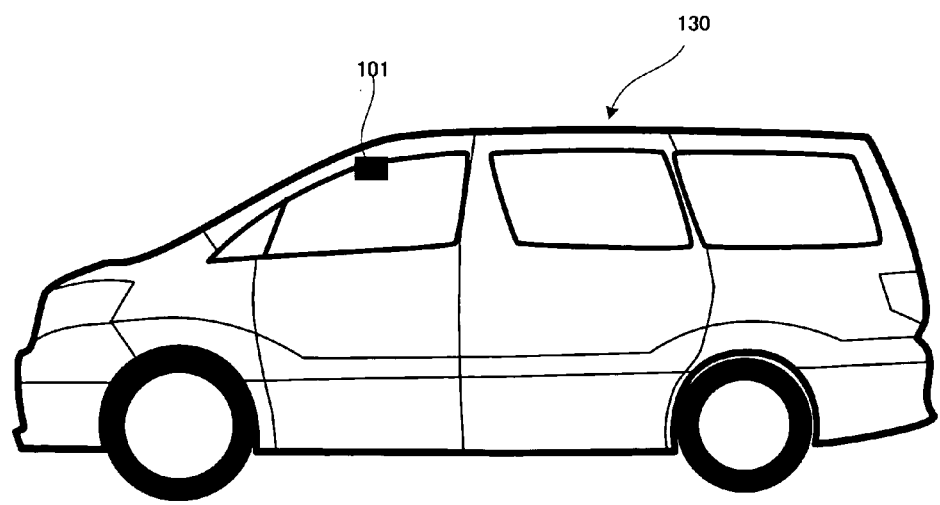

In FIG. 27, (a) illustrates an example of fitting an image pickup optical system 101 according to the present invention to the front side of an automobile 130, processing the images picked up by each of the image pickup optical systems 101 fitted to the automobile including the above-described one to correct distortions and displaying the images simultaneously. In FIG. 27, (b) illustrates an example of fitting a plurality of image pickup optical systems 101 according to the present invention respectively to various parts of an automobile 130 including corners and the top of the pole at the head of the automobile 130, processing the images picked up by each of the image pickup optical systems 101 to correct distortions and displaying the images simultaneously. The dimension of each of the imaging elements 50 is preferably made equal to the distance between the left margin and the right margin of the image A1 of the corresponding side view optical path A as described above by referring to (a) of FIG. 27 to obtain a horizontally broad view.

Figure 28:
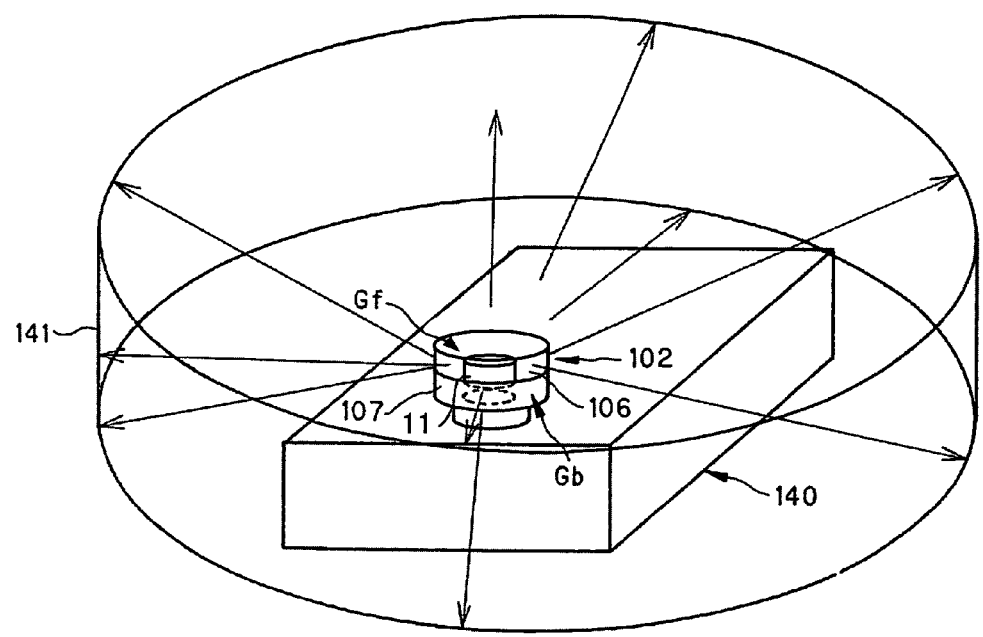
FIG. 28 is a schematic illustration of an example of using an optical system according to the present invention as a projection optical system of a projection apparatus.

FIG. 28 is a schematic illustration of an example of using a projection optical system 102 according to the present invention as a projection optical system of a projection apparatus 140. The picked up panoramic image is displayed on a display element arranged on the image plane 5 of the optical system and then a 360° omni-directional image is projected and displayed on a screen 141 arranged 360° omni-directionally by way of a projection optical system 102.

Figure 29:
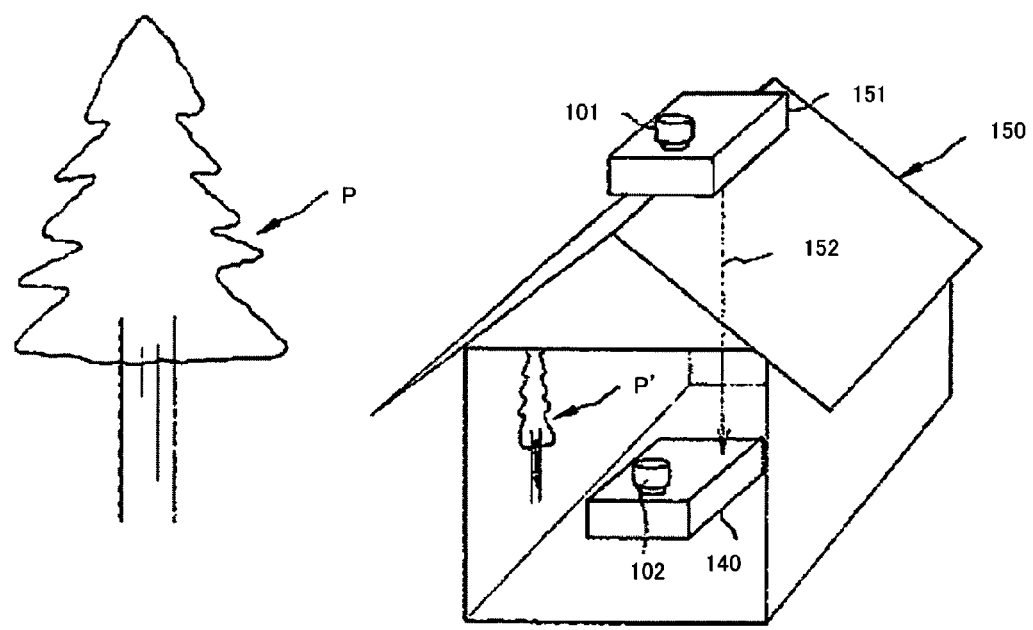
FIG. 29 is a schematic illustration of an example of using an optical system according to the present invention as an image pickup optical system for picking up an image of an outdoor object.

In the example of FIG. 29, an image pickup apparatus 151 including an image pickup optical system 101 according to the present invention is arranged at the outside of a building 150, while a projection apparatus 140 including another image pickup optical system 101 according to the present invention is arranged in the inside of the building and connected to the image pickup apparatus 151, and the image picked up by the image pickup apparatus 151 is sent to the projection apparatus 140 by way of an electric wire 152. An 360° omni-directional image of an outdoor object P is picked up by the image pickup apparatus 151 by way of the image pickup optical system 101 and the video signal of the picked up image is sent to the projection apparatus 140 by way of the electric wire 152 so that the image is displayed on the display element arranged on the image plane and then an enlarged image P' of the object P is projected and displayed on a wall in the building by way of the projection optical system 102.

The invention claimed is:

1. An optical element, that is part of an optical system, and that is made of a transparent medium that is rotationally symmetric relative to the central axis with a refractive index greater than 1, wherein
    the transparent medium has a first transmissive surface arranged at the outermost periphery relative to the central axis,
    a first reflective surface arranged at the side of the central axis relative to the first transmissive surface, a second reflective surface arranged at the side opposite to the image plane relative to the first reflective surface and a second transmissive surface arranged at the image plane side relative to the second reflective surface, that the flux of light entering the transparent medium goes into the transparent medium by way of the first transmissive surface so as to be reflected to the side opposite to the image plane by the first reflective surface and then to the image plane side by the second reflective surface to form an optical path before going out from the transparent medium at the image plane side by way of the second transmissive surface in the order of forward ray tracing and that the optical path is formed only at a side relative to the central axis, and the meridional cross section of the second transmissive surface represents negative power and that the optical element satisfies the condition of $$-10 < P2/Pm < -1 \tag{2},$$

where P2 is the power of the second transmissive surface and Pm is the power of the entire optical system in which the optical element is included at the meridional cross section of the central principal ray of light.

2. The optical element according to claim 1, wherein the transparent medium has a view angle of about 90° at a side in a cross section including the central axis thereof and as viewed from a direction orthogonal relative to the central axis, and the optical path includes a substantially v-shaped optical path.

3. The optical element according to claim 1, wherein the element satisfies the condition of $$0.01 < \beta\omega < 0.5 \tag{1},$$

where βω is the angular magnification of meridional cross section of the optical element.

4. The optical element according to claim 1, wherein the element is formed by a transparent medium having a refractive index not smaller than 1.5.

5. The optical element according to claim 1, wherein at least one of the first reflective surface and the second reflective surface has a total reflection effect.

6. The optical element according to claim 1, wherein at least one of the first reflective surface and the second reflective surface is formed by an extended rotary free curved surface formed by rotating a line segment of arbitrary shape having no plane of symmetry around the central axis.

7. The optical element according to claim 1, wherein at least one of the surfaces that the transparent medium has is formed by an extended rotary free curved surface formed by rotating a line segment of arbitrary shape including one or more than one odd-number-th degree terms.

8. An optical system having an optical element according to claim 1, wherein the system includes a front group, a back group arranged at the side of the image plane relative to the front group and an aperture arranged between the front group and the back group and that the optical element is arranged in the front group to form an image of an object arranged so as to surround the central axis or project an image of the object in a radial direction from the central axis.

9. The optical system according to claim 8, wherein the system forms an image of an annular object around the central axis in a plane orthogonal relative to the central axis.

10. The optical system according to claim 8, wherein the first reflective surface and the second reflective surface include concave surfaces directed to the aperture.

11. The optical system according to claim 8, wherein the second transmissive surface includes a concave surface directed to the aperture.

12. The optical system according to claim 8, wherein the system does not form any intermediate image on the optical path.

13. The optical system according to claim 8, wherein the optical element has a direct view optical path for observing the direct front of the optical element and a side view optical path for observing the direction that is orthogonal relative to the central axis and forms an image of the direct view optical path and an image of the side view optical path on the same plane.

14. The optical system according to claim 8, wherein the system satisfies the condition of $$D/Dr < 10 \tag{3},$$

where D is the external dimension of the optical element and Dr is the external dimension of the image.

15. The optical system according to claim 14, wherein the system satisfies the condition of $$D < 20 \text{ mm} \tag{4},$$

where D is the external dimension of the optical element.

16. An endoscope formed by using an optical system according to claim 8.

17. An optical element, that is part of an optical system, and that is made of a transparent medium that is rotationally symmetric relative to the central axis with a refractive index greater than 1, wherein the transparent medium has a first transmissive surface arranged at the outermost periphery relative to the central axis, a first reflective surface arranged at the side of the central axis relative to the first transmissive surface, a second reflective surface arranged at the image plane side relative to the first reflective surface, a third reflective surface arranged at the side opposite to the image plane relative to the second reflective surface and a second transmissive surface arranged at the image plane side relative to the third reflective surface, that the flux of light entering the transparent medium goes thereinto by way of the first transmissive surface so as to be reflected to the image plane side by the first reflective surface, then to the side opposite to the image plane by the second reflective surface and then to the image plane side by the third reflective surface to form an optical path before going out from the transparent medium at the image plane side by way of the second transmissive surface in the order of forward ray tracing and that the optical path is formed only at a side relative to the central axis, and the meridional cross section of the second transmissive surface represents negative power and that the optical element satisfies the condition of $$-10 < P2/Pm < -1 \tag{2},$$

where P2 is the power of the second transmissive surface and Pm is the power of the entire optical system in which the optical element is included at the meridional cross section of the central principal ray of light.

18. The optical element according to claim 17, wherein the transparent medium has a view angle of about 90° at a side in a cross section including the central axis thereof and as viewed from a direction orthogonal relative to the central axis, and the optical path is formed a substantially w-shaped optical path.

19. The optical element according to claim 17, wherein at least one of the first reflective surface, the second reflective surface and the third reflective surface has a total reflection effect.

20. The optical element according to claim 17, wherein at least one of the first reflective surface, the second reflective surface and the third reflective surface is formed by an extended rotary free curved surface formed by rotating a line segment of arbitrary shape having no plane of symmetry around the central axis.

21. An optical system having an optical element according to claim 17, wherein the system includes a front group, a back group arranged at the side of the image plane relative to the front group and an aperture arranged between the front group and the back group and that the optical element is arranged in the front group to form an image of an object arranged so as to surround the central axis or project an image of the object in a radial direction from the central axis.

22. The optical system according to claim 21, wherein the first reflective surface, the second reflective surface and the third reflective surface include convex surfaces directed to the aperture.

\* \* \* \* \*